United States Patent
Sharkey et al.

(10) Patent No.: US 7,267,683 B2
(45) Date of Patent: *Sep. 11, 2007

(54) METHOD FOR TREATING INTERVERTEBRAL DISCS

(75) Inventors: Hugh R. Sharkey, Woodside, CA (US); John Ashley, San Francisco, CA (US); Joel Saal, Portola Valley, CA (US); Jeffrey A. Saal, Portola Valley, CA (US); Le T. Le, San Jose, CA (US)

(73) Assignee: Oratec Interventions, Inc., Menlo Park, CA (US)

( * ) Notice: Subject to any disclaimer, the term of this patent is extended or adjusted under 35 U.S.C. 154(b) by 679 days.

This patent is subject to a terminal disclaimer.

(21) Appl. No.: 10/712,063

(22) Filed: Nov. 14, 2003

(65) Prior Publication Data

US 2004/0111136 A1 Jun. 10, 2004

Related U.S. Application Data

(60) Continuation of application No. 10/388,609, filed on (Continued)

(60) Provisional application No. 60/185,221, filed on Feb.

(Continued)

(51) Int. Cl.
*A61F 7/00* (2006.01)

(52) U.S. Cl. .......................... 607/96; 128/898; 606/41; 607/117

(58) Field of Classification Search .................. 607/96, 607/98–102, 117; 606/41, 47–50; 128/898
See application file for complete search history.

(56) References Cited

U.S. PATENT DOCUMENTS 164,184 A 6/1875 Kidder (Continued)

FOREIGN PATENT DOCUMENTS

CA 2188688 11/1995

(Continued)

OTHER PUBLICATIONS

Kirwin, Thomas J., "The Treatment of Prostatic Hypertrophy by a New 'Shrinkage'Method", J. Urol. vol. 32; 1934, pp. 481-494.*
Trimedyne, The Less Invasive Laser Advantage, Omni Spinal Introduction System.

(Continued)

*Primary Examiner*—Michael Peffley
(74) *Attorney, Agent, or Firm*—Fish & Richardson P.C.

(57) ABSTRACT

A device is described that may be positioned at a location in an intervertebral disc for diagnosis or treatment of the disc. Treatment may include, for example, applying energy or removing material, and may decrease intradiscal pressure. Radiofrequency energy may be applied. A percutaneous method of repairing a fissure in the annulus pulposus comprises placing an energy source adjacent to the fissure and providing sufficient energy to the fissure to raise the temperature to at least about 45-70° C. and for a sufficient time to cause the collagen to weld. An intervertebral fissure also can be treated by placing a catheter with a lumen adjacent to the fissure and injecting sealant into the fissure via the catheter, thereby sealing the fissure. An intervertebral fissure additionally can be treated by providing a catheter having a distal end, a proximal end, a longitudinal axis, and an intradiscal section at the catheter's distal end on which there is at least one functional element. The next step is applying a force longitudinally to the proximal of the catheter which is sufficient to advance the intradiscal section through the nucleus pulposus and around an inner wall of an annulus fibrosus, but which force is insufficient to puncture the annulus fibrosus. Next the functional element is positioned at a selected location of the disc by advancing or retracting the catheter and optionally twisting the proximal end of the catheter. Then the functional unit treats the annular fissure. Optionally, there is an additional step of adding a substance to seal the fissure. An externally guidable intervertebral disc apparatus also is disclosed.

28 Claims, 11 Drawing Sheets

Related U.S. Application Data

(60) Mar. 17, 2003, now Pat. No. 6,997,941, which is a continuation of application No. 09/707,627, filed on Nov. 6, 2000, now Pat. No. 6,547,810, which is a continuation of application No. 09/236,816, filed on Jan. 25, 1999, now Pat. No. 6,290,715, which is a continuation of application No. 09/162,704, filed on Sep. 29, 1998, now Pat. No. 6,099,514, and a continuation of application No. 09/153,552, filed on Sep. 15, 1998, now Pat. No. 6,126,682, and a continuation of application No. 08/881,525, filed on Jun. 24, 1997, now Pat. No. 6,122,549, and a continuation of application No. 08/881,692, filed on Jun. 24, 1997, now Pat. No. 6,073,051, and a continuation of application No. 08/881,527, filed on Jun. 24, 1997, now Pat. No. 5,980,504, and a continuation of application No. 08/881,693, filed on Jun. 24, 1997, now Pat. No. 6,007,570, and a continuation of application No. 08/881,694, filed on Jun. 24, 1997, now Pat. No. 6,095,149, application No. 10/712,063, which is a continuation-in-part of application No. 10/624,894, filed on Jul. 23, 2003, now abandoned, and a continuation-in-part of application No. 09/876,833, filed on Jun. 6, 2001, now Pat. No. 6,726,685, and a continuation-in-part of application No. 09/876,832, filed on Jun. 6, 2001, now Pat. No. 6,733,496, and a continuation-in-part of application No. 09/876,831, filed on Jun. 6, 2001, now Pat. No. 6,832,997, which is a division of application No. 09/753,786, filed on Jan. 2, 2001, now Pat. No. 6,645,203, which is a continuation-in-part of application No. 09/022,688, filed on Feb. 12, 1998, now Pat. No. 6,168,593, application No. 10/712,063, which is a continuation-in-part of application No. 10/242,777, filed on Sep. 13, 2002, now abandoned, which is a division of application No. 09/340,065, filed on Jun. 25, 1999, now Pat. No. 6,461,357, which is a continuation-in-part of application No. 09/022,612, filed on Feb. 12, 1998, now Pat. No. 6,135,999, application No. 10/712,063, which is a continuation-in-part of application No. 09/776,231, filed on Feb. 1, 2001, now Pat. No. 6,767,347, which is a division of application No. 09/272,806, filed on Mar. 19, 1999, now Pat. No. 6,258,086, application No. 10/712,063, which is a continuation-in-part of application No. 09/776,186, filed on Feb. 1, 2001, now Pat. No. 6,749,605, which is a division of application No. 09/272,806, application No. 10/712,063, which is a continuation-in-part of application No. 09/884,859, filed on Jun. 18, 2001, now Pat. No. 6,878,155, which is a continuation of application No. 09/792,628, filed on Feb. 22, 2001, now Pat. No. 7,069,087, application No. 10/712,063, which is a continuation-in-part of application No. 09/664,473, filed on Sep. 18, 2000, which is a continuation of application No. 08/696,051, filed on Aug. 13, 1996, now abandoned.

(60) 25, 2000, provisional application No. 60/078,545, filed on Mar. 19, 1998, provisional application No. 60/047,820, filed on May 28, 1997, provisional application No. 60/047,841, filed on May 28, 1997, provisional application No. 60/047,818, filed on May 28, 1997, provisional application No. 60/047,848, filed on May 28, 1997, provisional application No. 60/045,941, filed on May 8, 1997, provisional application No. 60/037,620, filed on Feb. 12, 1997, provisional application No. 60/037,782, filed on Feb. 12, 1997, provisional application No. 60/029,734, filed on Oct. 23, 1996, provisional application No. 60/029,735, filed on Oct. 23, 1996, provisional application No. 60/029,600, filed on Oct. 23, 1996.

(56) References Cited

U.S. PATENT DOCUMENTS

| | | |
|---|---|---|
| 300,155 A | 6/1884 | Starr |
| 371,664 A | 10/1887 | Brannan et al. |
| 452,220 A | 5/1891 | Gunning |
| 1,314,855 A | 9/1919 | Carpenter |
| 1,366,756 A | 1/1921 | Wappler |
| 1,731,627 A | 10/1929 | Johnson et al. |
| 1,735,271 A | 11/1929 | Groff |
| 1,814,791 A | 7/1931 | Ende |
| 1,908,583 A | 5/1933 | Wappler |
| 1,916,722 A | 7/1933 | Ende |
| 1,932,258 A | 10/1933 | Wappler |
| 1,943,543 A | 1/1934 | McFadden |
| 1,983,669 A | 12/1934 | Kimble |
| 2,002,594 A | 5/1935 | Wappler et al. |
| 2,004,559 A | 6/1935 | Wappler et al. |
| 2,050,904 A | 8/1936 | Trice |
| 2,056,377 A | 10/1936 | Wappler |
| 2,090,923 A | 8/1937 | Wappler |
| 2,224,464 A | 12/1940 | Wolf |
| 2,275,167 A | 3/1942 | Bierman |
| 2,888,928 A | 6/1959 | Seiger |
| 3,152,590 A | 10/1964 | Rodriguez Zurdo et al. |
| 3,163,165 A | 12/1964 | Isikawa |
| 3,178,728 A | 4/1965 | Christensen |
| 3,460,539 A | 8/1969 | Anhalt |
| 3,579,643 A | 5/1971 | Morgan |
| 3,595,239 A | 7/1971 | Petersen |
| 3,655,032 A | 4/1972 | Willis |
| 3,768,482 A | 10/1973 | Shaw |
| 3,769,984 A | 11/1973 | Muench |
| 3,776,230 A | 12/1973 | Neefe |
| 3,801,766 A | 4/1974 | Morrison |
| 3,807,390 A | 4/1974 | Ostrowski et al. |
| 3,815,604 A | 6/1974 | O'Malley et al. |
| 3,828,780 A | 8/1974 | Morrison |
| 3,856,015 A | 12/1974 | Iglesias |
| 3,867,728 A | 2/1975 | Substad et al. |
| 3,870,047 A | 3/1975 | Gonser |
| 3,879,767 A | 4/1975 | Substad |
| 3,886,600 A | 6/1975 | Kahn et al. |
| 3,901,242 A | 8/1975 | Storz |
| 3,902,494 A | 9/1975 | Haberlen et al. |
| 3,920,021 A | 11/1975 | Hiltebrandt |
| 3,920,022 A | 11/1975 | Pastor |
| 3,938,198 A | 2/1976 | Kahn et al. |
| 3,938,527 A | 2/1976 | Rioux et al. |
| 3,945,375 A | 3/1976 | Banko |
| 3,970,088 A | 7/1976 | Morrison |
| 3,987,499 A | 10/1976 | Scharbach et al. |
| 3,987,795 A | 10/1976 | Morrison |
| 3,992,725 A | 11/1976 | Homsy |
| 4,011,872 A | 3/1977 | Komiya |
| 4,016,881 A | 4/1977 | Roiux et al. |
| 4,034,762 A | 7/1977 | Corsens et al. |
| 4,040,426 A | 8/1977 | Morrison |
| 4,043,342 A | 8/1977 | Morrison, Jr. |
| 4,060,086 A | 11/1977 | Storz |
| 4,060,087 A | 11/1977 | Hiltebrandt et al. |
| 4,060,088 A | 11/1977 | Morrison |
| 4,074,718 A | 2/1978 | Morrison, Jr. |
| 4,085,466 A | 4/1978 | Goodfellow et al. |
| 4,116,198 A | 9/1978 | Roos |

| Patent Number | Date | Inventor |
|---|---|---|
| 4,129,470 A | 12/1978 | Homsy |
| 4,134,406 A | 1/1979 | Iglesias |
| 4,140,130 A | 2/1979 | Storm, III |
| 4,170,234 A | 10/1979 | Graham |
| 4,181,131 A | 1/1980 | Ogiu |
| 4,184,492 A | 1/1980 | Meinke et al. |
| 4,224,696 A | 9/1980 | Murray et al. |
| 4,224,697 A | 9/1980 | Murray et al. |
| 4,240,441 A | 12/1980 | Khalil |
| 4,301,802 A | 11/1981 | Poler |
| 4,326,529 A | 4/1982 | Doss et al. |
| 4,344,193 A | 8/1982 | Kenny |
| 4,362,160 A | 12/1982 | Hiltebrandt |
| 4,375,220 A | 3/1983 | Matvias |
| 4,381,007 A | 4/1983 | Doss |
| 4,397,314 A | 8/1983 | Vaguine |
| 4,405,314 A | 9/1983 | Cope |
| 4,411,266 A | 10/1983 | Cosman |
| 4,418,692 A | 12/1983 | Guay |
| 4,427,006 A | 1/1984 | Nottke |
| 4,448,198 A | 5/1984 | Turner |
| 4,476,862 A | 10/1984 | Pao |
| 4,478,822 A | 10/1984 | Haslam et al. |
| 4,483,338 A | 11/1984 | Bloom et al. |
| 4,517,965 A | 5/1985 | Ellison |
| 4,517,975 A | 5/1985 | Garito et al. |
| 4,524,770 A | 6/1985 | Orandi |
| 4,545,374 A | 10/1985 | Jacobson |
| 4,559,951 A | 12/1985 | Dahl et al. |
| 4,562,838 A | 1/1986 | Walker |
| 4,565,200 A | 1/1986 | Cosman |
| 4,590,934 A | 5/1986 | Malis et al. |
| 4,593,691 A | 6/1986 | Lindstrom et al. |
| 4,597,379 A | 7/1986 | Kihn et al. |
| 4,601,705 A | 7/1986 | McCoy |
| 4,643,186 A | 2/1987 | Rosen et al. |
| 4,646,737 A | 3/1987 | Hussein et al. |
| 4,651,734 A | 3/1987 | Doss et al. |
| 4,672,962 A | 6/1987 | Hershenson |
| 4,682,596 A | 7/1987 | Bales et al. |
| 4,688,569 A | 8/1987 | Rabinowitz |
| 4,699,157 A | 10/1987 | Shonk |
| 4,712,559 A | 12/1987 | Turner |
| 4,719,914 A | 1/1988 | Johnson |
| 4,735,201 A | 4/1988 | O'Reilly |
| 4,737,146 A | 4/1988 | Amaki et al. |
| 4,753,223 A | 6/1988 | Bremer |
| 4,754,752 A | 7/1988 | Ginsburg et al. |
| 4,765,331 A | 8/1988 | Petruzzi et al. |
| 4,769,005 A | 9/1988 | Ginsburg et al. |
| 4,784,161 A | 11/1988 | Skalsky et al. |
| 4,800,899 A | 1/1989 | Elliott |
| 4,805,616 A | 2/1989 | Pao |
| 4,811,733 A | 3/1989 | Borsanyi et al. |
| 4,811,743 A | 3/1989 | Stevens |
| 4,815,462 A | 3/1989 | Clark |
| 4,823,791 A | 4/1989 | D'Amelio et al. |
| 4,838,859 A | 6/1989 | Strassmann |
| 4,846,175 A | 7/1989 | Frimberger |
| 4,860,744 A | 8/1989 | Johnson et al. |
| 4,863,430 A | 9/1989 | Klyce et al. |
| 4,873,976 A | 10/1989 | Schreiber |
| 4,894,063 A | 1/1990 | Nashef |
| 4,895,148 A | 1/1990 | Bays et al. |
| 4,907,585 A | 3/1990 | Schachar |
| 4,907,589 A | 3/1990 | Cosman |
| 4,917,092 A | 4/1990 | Todd et al. |
| 4,919,129 A | 4/1990 | Weber et al. |
| 4,924,865 A | 5/1990 | Bays et al. |
| 4,924,882 A | 5/1990 | Donovan |
| 4,927,420 A | 5/1990 | Newkirk et al. |
| 4,936,301 A | 6/1990 | Rexroth et al. |
| RE33,258 E | 7/1990 | Onik et al. |
| 4,943,290 A | 7/1990 | Rexroth et al. |
| 4,944,727 A | 7/1990 | McCoy |
| 4,950,234 A | 8/1990 | Fujioka et al. |
| 4,950,267 A | 8/1990 | Ishihara et al. |
| 4,955,378 A | 9/1990 | Grasso |
| 4,955,882 A | 9/1990 | Hakky |
| 4,966,597 A | 10/1990 | Cosman |
| 4,976,709 A | 12/1990 | Sand |
| 4,976,711 A | 12/1990 | Parins et al. |
| 4,976,715 A | 12/1990 | Bays et al. |
| 4,998,933 A | 3/1991 | Eggers et al. |
| 5,007,908 A | 4/1991 | Rydell |
| 5,009,656 A | 4/1991 | Reimels |
| 5,013,312 A | 5/1991 | Parins et al. |
| 5,084,043 A | 1/1992 | Hertzmann et al. |
| 5,084,044 A | 1/1992 | Quint |
| 5,085,657 A | 2/1992 | Ben-Simhon |
| 5,085,659 A | 2/1992 | Rydell |
| 5,098,430 A | 3/1992 | Fleenor |
| 5,100,402 A | 3/1992 | Fan |
| 5,103,804 A | 4/1992 | Abele et al. |
| RE33,925 E | 5/1992 | Bales et al. |
| 5,114,402 A | 5/1992 | McCoy |
| 5,122,138 A | 6/1992 | Manwaring |
| 5,125,928 A | 6/1992 | Parins et al. |
| 5,129,889 A | 7/1992 | Hahn et al. |
| 5,152,748 A | 10/1992 | Chastagner |
| 5,158,561 A | 10/1992 | Rydell et al. |
| 5,163,938 A | 11/1992 | Kambara et al. |
| 5,171,255 A | 12/1992 | Rydell |
| 5,178,620 A | 1/1993 | Eggers et al. |
| 5,186,181 A | 2/1993 | Franconi et al. |
| 5,191,883 A | 3/1993 | Lennox et al. |
| 5,192,267 A | 3/1993 | Shapira et al. |
| 5,195,541 A | 3/1993 | Obenchain |
| 5,201,729 A | 4/1993 | Hertzmann et al. |
| 5,201,730 A | 4/1993 | Easley et al. |
| 5,201,731 A | 4/1993 | Hakky |
| 5,205,816 A | 4/1993 | Dodson et al. |
| 5,207,675 A | 5/1993 | Canady |
| 5,211,625 A | 5/1993 | Sakurai et al. |
| 5,213,097 A | 5/1993 | Zeindler |
| 5,230,334 A | 7/1993 | Klopotek |
| 5,241,972 A | 9/1993 | Bonati |
| 5,242,439 A | 9/1993 | Larsen et al. |
| 5,242,441 A | 9/1993 | Avirall |
| 5,254,121 A | 10/1993 | Manevitz et al. |
| 5,261,906 A | 11/1993 | Pennino et al. |
| 5,267,994 A | 12/1993 | Gentelia et al. |
| 5,273,524 A | 12/1993 | Fox et al. |
| 5,275,151 A | 1/1994 | Shockey et al. |
| 5,277,696 A | 1/1994 | Hagen |
| 5,279,559 A | 1/1994 | Barr |
| 5,281,213 A | 1/1994 | Milder et al. |
| 5,281,218 A | 1/1994 | Imran |
| 5,282,845 A | 2/1994 | Bush et al. |
| 5,284,479 A | 2/1994 | de Jong |
| 5,285,795 A | 2/1994 | Ryan et al. |
| 5,300,069 A | 4/1994 | Hunsberger et al. |
| 5,301,687 A | 4/1994 | Wong et al. |
| 5,304,169 A | 4/1994 | Sand |
| 5,308,311 A | 5/1994 | Eggers et al. |
| 5,311,858 A | 5/1994 | Adair |
| 5,313,962 A | 5/1994 | Obenchain |
| 5,318,525 A | 6/1994 | West et al. |
| 5,320,115 A | 6/1994 | Kenna |
| 5,323,778 A | 6/1994 | Kandarpa et al. |
| 5,334,193 A | 8/1994 | Nardella |
| 5,336,222 A | 8/1994 | Durgin et al. |
| 5,342,357 A | 8/1994 | Nardella |
| 5,345,945 A | 9/1994 | Hodgson et al. |
| 5,348,554 A | 9/1994 | Imran et al. |
| 5,352,868 A | 10/1994 | Denen et al. |

| | | | | | |
|---|---|---|---|---|---|
| 5,354,331 A | 10/1994 | Schachar | 5,676,662 A | 10/1997 | Fleischhacker et al. |
| 5,364,395 A | 11/1994 | West, Jr. | 5,680,860 A | 10/1997 | Imran |
| 5,364,839 A | 11/1994 | Gerhart et al. | 5,681,282 A | 10/1997 | Eggers et al. |
| 5,366,443 A | 11/1994 | Eggers et al. | 5,683,366 A | 11/1997 | Eggers et al. |
| 5,366,490 A | 11/1994 | Edwards et al. | 5,683,384 A | 11/1997 | Gough et al. |
| 5,382,247 A | 1/1995 | Cimino et al. | 5,687,723 A | 11/1997 | Avitall |
| 5,383,876 A | 1/1995 | Nardella | 5,688,267 A | 11/1997 | Panescu et al. |
| 5,383,923 A | 1/1995 | Webster | 5,688,270 A | 11/1997 | Yates et al. |
| 5,385,148 A | 1/1995 | Lesh et al. | 5,693,050 A | 12/1997 | Speiser |
| 5,389,100 A | 2/1995 | Bacich et al. | 5,694,945 A | 12/1997 | Ben-Haim |
| 5,396,900 A | 3/1995 | Slater et al. | 5,697,281 A | 12/1997 | Eggers et al. |
| 5,397,304 A | 3/1995 | Truckai | 5,697,536 A | 12/1997 | Eggers et al. |
| 5,401,272 A | 3/1995 | Perkins | 5,697,882 A | 12/1997 | Eggers et al. |
| 5,403,311 A | 4/1995 | Abele et al. | 5,697,909 A | 12/1997 | Eggers et al. |
| 5,409,008 A | 4/1995 | Svenson et al. | 5,697,927 A | 12/1997 | Imran et al. |
| 5,415,633 A | 5/1995 | Lazarus et al. | 5,700,262 A | 12/1997 | Acosta et al. |
| 5,421,819 A | 6/1995 | Edwards et al. | 5,718,702 A | 2/1998 | Edwards |
| 5,423,806 A | 6/1995 | Dale et al. | 5,735,792 A | 4/1998 | Vander Hoek et al. |
| 5,423,808 A | 6/1995 | Edwards et al. | 5,738,683 A | 4/1998 | Osypka |
| 5,423,811 A | 6/1995 | Imran et al. | 5,741,245 A | 4/1998 | Cozean et al. |
| 5,423,815 A | 6/1995 | Fugo | 5,743,903 A | 4/1998 | Stern et al. |
| 5,423,882 A | 6/1995 | Jackman et al. | 5,762,626 A | 6/1998 | Lundquist et al. |
| 5,431,649 A | 7/1995 | Mulier et al. | 5,766,153 A | 6/1998 | Eggers et al. |
| 5,433,708 A | 7/1995 | Nichols et al. | 5,779,646 A | 7/1998 | Koblish et al. |
| 5,433,739 A * | 7/1995 | Sluijter et al. ............. 607/99 | 5,779,699 A | 7/1998 | Lipson |
| 5,437,661 A | 8/1995 | Rieser | 5,782,795 A | 7/1998 | Bays |
| 5,437,662 A | 8/1995 | Nardella | 5,785,705 A | 7/1998 | Baker |
| 5,437,664 A | 8/1995 | Cohen et al. | 5,797,903 A | 8/1998 | Swanson et al. |
| 5,441,499 A | 8/1995 | Fritzsch | 5,807,306 A | 9/1998 | Shapland et al. |
| 5,451,223 A | 9/1995 | Ben-Simhon | 5,810,802 A | 9/1998 | Panescu et al. |
| 5,454,809 A | 10/1995 | Janssen | 5,810,809 A | 9/1998 | Rydell |
| 5,456,682 A | 10/1995 | Edwards et al. | 5,836,875 A | 11/1998 | Webster |
| 5,458,596 A | 10/1995 | Lax et al. | 5,836,892 A | 11/1998 | Lorenzo |
| 5,458,597 A | 10/1995 | Edwards et al. | 5,836,947 A | 11/1998 | Fleischman et al. |
| 5,464,023 A | 11/1995 | Viera | 5,853,409 A | 12/1998 | Swanson et al. |
| 5,465,737 A | 11/1995 | Schachar | 5,857,991 A | 1/1999 | Grothoff et al. |
| 5,470,309 A | 11/1995 | Edwards et al. | 5,860,951 A | 1/1999 | Eggers et al. |
| 5,472,426 A | 12/1995 | Bonati et al. | 5,860,974 A | 1/1999 | Abele |
| 5,472,441 A | 12/1995 | Edwards et al. | 5,861,002 A | 1/1999 | Desai |
| 5,484,403 A | 1/1996 | Yoakum et al. | 5,871,469 A | 2/1999 | Eggers et al. |
| 5,484,432 A | 1/1996 | Sand | 5,871,501 A | 2/1999 | Leschinsky et al. |
| 5,484,435 A | 1/1996 | Fleenor et al. | 5,873,855 A | 2/1999 | Eggers et al. |
| 5,486,161 A | 1/1996 | Lax et al. | 5,874,500 A | 2/1999 | Rhee et al. |
| 5,487,385 A | 1/1996 | Avitall | 5,882,346 A | 3/1999 | Pomeranz et al. |
| 5,487,757 A | 1/1996 | Truckai et al. | 5,885,217 A | 3/1999 | Gisselberg et al. |
| 5,498,258 A | 3/1996 | Hakky et al. | 5,885,278 A | 3/1999 | Fleischman |
| 5,500,012 A | 3/1996 | Brucker et al. | 5,888,198 A | 3/1999 | Eggers et al. |
| 5,507,812 A | 4/1996 | Moore | 5,888,220 A | 3/1999 | Felt et al. |
| 5,514,130 A | 5/1996 | Baker | 5,891,095 A | 4/1999 | Eggers et al. |
| 5,520,645 A | 5/1996 | Imran et al. | 5,897,553 A | 4/1999 | Mulier et al. |
| 5,522,815 A | 6/1996 | Durgin | 5,902,272 A | 5/1999 | Eggers et al. |
| 5,524,338 A | 6/1996 | Martyniuk et al. | 5,910,129 A | 6/1999 | Koblish et al. |
| 5,527,331 A | 6/1996 | Kresch et al. | 5,916,158 A | 6/1999 | Webster |
| 5,540,681 A | 7/1996 | Strul et al. | 5,916,166 A | 6/1999 | Reiss |
| 5,542,920 A | 8/1996 | Cherif Cheikh | 5,921,924 A | 7/1999 | Avitall |
| 5,542,945 A | 8/1996 | Fritzsch | 5,935,123 A | 8/1999 | Edwards et al. |
| 5,545,161 A | 8/1996 | Imran | 5,948,008 A | 9/1999 | Daikuzono |
| 5,545,193 A | 8/1996 | Fleischman et al. | 5,976,105 A | 11/1999 | Marcove et al. |
| 5,569,242 A | 10/1996 | Lax et al. | 5,980,471 A | 11/1999 | Jafari |
| 5,569,244 A | 10/1996 | Hahnen | 5,980,504 A | 11/1999 | Sharkey et al. |
| 5,569,245 A | 10/1996 | Guglielmi et al. | 5,991,650 A | 11/1999 | Swanson et al. |
| 5,571,147 A | 11/1996 | Sluijter et al. | 5,993,424 A | 11/1999 | Lorenzo et al. |
| 5,573,533 A | 11/1996 | Strul | 6,004,319 A | 12/1999 | Goble et al. |
| 5,582,609 A | 12/1996 | Swanson et al. | 6,007,570 A | 12/1999 | Sharkey et al. |
| 5,584,830 A | 12/1996 | Ladd et al. | 6,010,493 A | 1/2000 | Snoke |
| 5,599,346 A | 2/1997 | Edwards et al. | 6,014,579 A | 1/2000 | Pomeranz et al. |
| 5,601,572 A | 2/1997 | Middleman et al. | 6,017,361 A | 1/2000 | Mikus et al. |
| 5,603,709 A | 2/1997 | Johnson | 6,023,638 A | 2/2000 | Swanson |
| 5,607,422 A | 3/1997 | Smeets et al. | 6,033,397 A | 3/2000 | Laufer et al. |
| 5,630,839 A | 5/1997 | Corbett, III et al. | 6,036,688 A | 3/2000 | Edwards |
| 5,637,090 A | 6/1997 | McGee et al. | 6,048,329 A | 4/2000 | Thompson et al. |
| 5,643,255 A | 7/1997 | Organ | 6,048,340 A | 4/2000 | Miyagi |
| 5,673,707 A | 10/1997 | Chandrasekaran | 6,053,172 A | 4/2000 | Hovda et al. |

| | | | | | | |
|---|---|---|---|---|---|---|
| 6,056,744 | A | 5/2000 | Edwards | EP | 0 274 705 | | 7/1988 |
| 6,073,051 | A | 6/2000 | Sharkey et al. | EP | 0 274 705 | A1 | 7/1988 |
| 6,079,417 | A | 6/2000 | Fugo | EP | 0 392 837 | | 10/1990 |
| 6,093,185 | A | 7/2000 | Ellis et al. | EP | 0 407 057 | | 1/1991 |
| 6,095,149 | A | 8/2000 | Sharkey et al. | EP | 0 439 263 | | 7/1991 |
| 6,099,514 | A | 8/2000 | Sharkey et al. | EP | 0 479 482 | A1 | 4/1992 |
| 6,102,046 | A | 8/2000 | Weinstein et al. | EP | 0 521 595 | | 1/1993 |
| 6,105,581 | A | 8/2000 | Eggers et al. | EP | 0 521 595 | A2 | 1/1993 |
| 6,106,522 | A | 8/2000 | Fleischman et al. | EP | 0 542 412 | A1 | 5/1993 |
| 6,113,591 | A | 9/2000 | Whayne et al. | EP | 0 558 297 | A2 | 9/1993 |
| 6,122,549 | A | 9/2000 | Sharkey et al. | EP | 0 566 450 | A1 | 10/1993 |
| 6,126,682 | A | 10/2000 | Sharkey et al. | EP | 0 572 131 | A1 | 12/1993 |
| 6,135,999 | A | 10/2000 | Fanton et al. | EP | 0 648 475 | | 4/1995 |
| 6,165,139 | A | 12/2000 | Damadian | EP | 0 682 910 | | 11/1995 |
| 6,168,593 | B1 | 1/2001 | Sharkey et al. | EP | 0 682 910 | A1 | 11/1995 |
| 6,171,306 | B1 | 1/2001 | Swanson et al. | EP | 0 479 482 | B1 | 5/1996 |
| 6,176,857 | B1 | 1/2001 | Ashley | EP | 0 729 730 | A1 | 9/1996 |
| 6,179,836 | B1 | 1/2001 | Eggers et al. | EP | 0 737 487 | | 10/1996 |
| 6,203,525 | B1 | 3/2001 | Whayne et al. | EP | 0 737 487 | A2 | 10/1996 |
| 6,217,528 | B1 | 4/2001 | Koblish et al. | EP | 0 783 903 | A1 | 7/1997 |
| 6,224,592 | B1 | 5/2001 | Eggers et al. | FR | 1122634 | | 9/1956 |
| 6,241,754 | B1 | 6/2001 | Swanson et al. | FR | 2 313 949 | | 1/1977 |
| 6,245,061 | B1 | 6/2001 | Panescu et al. | FR | 2645008 | | 3/1989 |
| 6,245,069 | B1 | 6/2001 | Gminder | GB | 1340451 | | 12/1973 |
| 6,258,086 | B1 | 7/2001 | Ashley et al. | GB | 1583397 | | 1/1981 |
| 6,261,311 | B1 | 7/2001 | Sharkey et al. | GB | 2160102 | | 12/1985 |
| 6,264,650 | B1 | 7/2001 | Hovda et al. | GB | 2164473 | | 3/1986 |
| 6,264,651 | B1 | 7/2001 | Underwood et al. | JP | 5-42166 | | 5/1993 |
| 6,270,476 | B1 | 8/2001 | Santoianni et al. | RU | 2 012 388 | | 5/1994 |
| 6,273,886 | B1 | 8/2001 | Edwards et al. | SU | 637118 | | 12/1978 |
| 6,277,112 | B1 | 8/2001 | Underwood et al. | WO | WO81/03271 | | 11/1981 |
| 6,283,960 | B1 | 9/2001 | Ashley | WO | WO82/02488 | | 8/1982 |
| 6,283,961 | B1 | 9/2001 | Underwood et al. | WO | WO84/03829 | | 10/1984 |
| 6,287,306 | B1 | 9/2001 | Kroll et al. | WO | WO85/02762 | | 7/1985 |
| 6,290,715 | B1 | 9/2001 | Sharkey et al. | WO | WO 92/05828 | | 4/1992 |
| 6,304,785 | B1 | 10/2001 | McCreery et al. | WO | WO92/05828 | | 4/1992 |
| 6,308,091 | B1 | 10/2001 | Avitall | WO | WO92/10142 | | 6/1992 |
| 6,332,880 | B1 | 12/2001 | Yang et al. | WO | WO93/01774 | | 2/1993 |
| 6,350,262 | B1 | 2/2002 | Ashley | WO | WO93/15664 | | 8/1993 |
| 6,355,032 | B1 | 3/2002 | Hovda et al. | WO | WO93/16648 | | 9/1993 |
| 6,379,350 | B1 | 4/2002 | Sharkey et al. | WO | WO93/20984 | | 10/1993 |
| 6,416,508 | B1 | 7/2002 | Eggers et al. | WO | WO94/10921 | | 5/1994 |
| 6,428,512 | B1 | 8/2002 | Anderson et al. | WO | WO95/01814 | | 1/1995 |
| 6,440,127 | B2 | 8/2002 | McGovern et al. | WO | WO95/10225 | | 4/1995 |
| 6,440,129 | B1 | 8/2002 | Simpson | WO | WO95/10321 | | 4/1995 |
| 6,461,357 | B1 | 10/2002 | Sharkey et al. | WO | WO95/10981 | | 4/1995 |
| 6,547,810 | B1 | 4/2003 | Sharkey et al. | WO | WO95/13113 | | 5/1995 |
| 6,562,028 | B2 | 5/2003 | Nield et al. | WO | WO95/18575 | | 7/1995 |
| 6,604,003 | B2 | 8/2003 | Fredricks et al. | WO | WO95/20360 | | 8/1995 |
| 6,638,276 | B2 | 10/2003 | Sharkey et al. | WO | WO95/25471 | | 9/1995 |
| 6,645,203 | B2 | 11/2003 | Sharkey et al. | WO | WO95/30373 | | 11/1995 |
| 2001/0023348 | A1 | 9/2001 | Ashley et al. | WO | WO95/30377 | | 11/1995 |
| 2001/0029370 | A1 | 10/2001 | Hodva et al. | WO | WO95/34259 | | 12/1995 |
| 2001/0031963 | A1 | 10/2001 | Sharkey et al. | WO | WO96/00036 | | 1/1996 |
| 2002/0019626 | A1 | 2/2002 | Sharkey et al. | WO | WO96/00040 | | 1/1996 |
| 2002/0022830 | A1 | 2/2002 | Sharkey et al. | WO | WO96/11638 | | 4/1996 |
| 2002/0120259 | A1 | 8/2002 | Lettice et al. | WO | WO96/29946 | | 10/1996 |
| 2002/0188284 | A1 | 12/2002 | To et al. | WO | WO96/32051 | | 10/1996 |
| 2002/188291 | A1 | 12/2002 | Uchida et al. | WO | WO96/32885 | | 10/1996 |
| 2003/0014050 | A1 | 1/2003 | Sharkey et al. | WO | WO96/34559 | | 11/1996 |
| | | | | WO | WO96/34568 | | 11/1996 |

FOREIGN PATENT DOCUMENTS

| | | | |
|---|---|---|---|
| WO | WO 96/34571 | | 11/1996 |
| WO | WO96/34571 | | 11/1996 |
| DE | 35 111 07 | | 10/1986 |
| WO | WO96/37146 | | 11/1996 |
| DE | 36 321 97 | | 3/1988 |
| WO | WO96/39085 | | 12/1996 |
| DE | 3918316 | | 3/1990 |
| WO | WO96/39914 | | 12/1996 |
| DE | 38 38 840 | | 5/1990 |
| WO | WO96/39966 | | 12/1996 |
| DE | 41 08 269 | | 6/1992 |
| WO | WO97/06855 | | 2/1997 |
| DE | 44 25 015 | | 1/1996 |
| WO | WO97/07468 | | 2/1998 |
| DE | 196 30 601 | | 2/1997 |
| WO | WO98/11944 | | 3/1998 |
| EP | 0 013 605 | | 7/1980 |
| WO | WO98/17190 | | 4/1998 |
| EP | 0 257 116 | | 3/1988 |
| WO | WO98/34558 | | 8/1998 |
| EP | 0 257 116 A1 | | 3/1988 |
| WO | WO99/18878 | | 4/1999 |

| | | |
|---|---|---|
| WO | WO99/47058 | 9/1999 |
| WO | WO99/51149 | 10/1999 |

OTHER PUBLICATIONS

PRNewswire (Dec. 12, 1994), Two Physicians Perform First Outpatient Cervical Disc Procedure Using Laser Technology.
Introduction to the LDD Disc Kit, Oct. 16, 1996.
Mayer et al., Lasers in Percutaneous Disc Surgery: Beneficial Technology or Gimmick?, vol. 25 No. 251 (1993) pp. 38-44.
Schatz et al., Preliminary Experience With Percutaneous Laser Disc Decompression in the Treatment of Sciatica, vol. 38 No. Oct. 5, 1995, pp. 432-436.
Savitz M. A., Same-day Microsurgical Arthroscopic lateral-approach Laser-assisted (SMALL) Fluoroscopic Discectomy, vol. 80, Jun. 1994 pp. 1039-1045.
Bosacco et al., Functional Results of Percutaneous Laser Disectomy, Dec. 1996, pp. 825-828.
Sluijter M.E., The Use of Radiofrequency lesions For Pain Relief in Failed Back Patients, vol. 10 No. 1 (1988).
Cosman et al., Theoretical Aspects of Radiofrequency lesions in the Dorsal Root Entry Zone, vol. 15 No. 6 (1984) pp. 945-950.
Wilkins et al., Neurosurgery: Method of Making Nervous System Lesions, ch. 337, pp. 2490-2499.
Yonezawa et al., The System and Procedure of percutaneous Intradiscal Laser Nucleotomy, vol. 15 No. 5 (1990) pp. 1175-1185.
Gottlob et al., Lasers in Surgery and Medicine: Holmium: YAG Laser Ablation of Human Intervertebral Disc: Preliminary Evaluation, vol. 12, (1991) pp. 86-91.
Buchelt et al., Laser in Surgery and Medicine: Fluorescence Guided Excimer Laser Ablation of Intervertebral Discs In Vitro, vol. 11, (1991) pp. 280-286.
Choy et al., Percutaneous Laser Disc Decompression: A New Therapeutic Modality, vol. 17 No. 8, (1992) pp. 949-956.
Sluijter et al., Persistant Pain Modern Methods of Treatment: Treatment of Chronic Back and neck Pain, vol. 3, (1981) pp. 141-179.
Sluijter, Int Disabil Studies: The use of Radio Frequency Lesions For Pain Relief in Failed Back, vol. 10, Sep. 4, 1996, pp. 141-179.
Shatz et al., CJS JCC Preliminary Experience With Percutaneous Laser Disc Decompression in the Treatment of Sciatica, vol. 38 No. 5, Oct. 1995 pp. 432-436.
Sluyter, Radiofrequency Lesions in the Treatment of Cervical Pain Syndromes, Radionics, Inc. (1989).
Kelly L.E., Purification and Properties of a 23kDa Ca2+-binding Protein, (1990) 271, pp. 661-666.
Gehring W. J., Exploring the Homeobox, (1993), pp. 215-221.
Buchelt et al., Lasers in Surgery and Medicine:Erb:YAG and Hol:YAG Laser Ablation of Meniscus and Intervertebral Discs, vol. 12 No. 4, (1992) pp. 375-381.
Leu et al., Der Orthopade: Endoskopie der Wirbelsaule: Minimalinvasive Therapie, vol. 21, (1992) pp. 267-272.
Phillips et al., JMRI: MR Imaging of Ho: YAG Laser Diskectomy with Histologic Correlation, vol. 3 No. 3, May/Jun. 1993.
Bromm et al., Human Neurobiology: Nerve Fibre Discharges, Cerebral Potentials and Sensations Induced by CO2 laser Stimulation, vol. 3, (1984) pp. 33-40.
Kolarik et al., Photonucleolysis of Intervertebral Disc and it's Herniation, vol. 51, (1990) pp. 69-71.
Wolgin et al., Excimer Ablation of Human Intervertbral Disc at 308 Nanometers, vol. 9, (1989) pp. 124-131.
Davis, Early experience with Laser Disc Decompression, vol. 79 No. 1, (1992) j. Florida M.A.
Quigley et al., Laser Discectomy: Comparison of System, vol. 19 No. 3 (1994) pp. 319-322.
Mehta et al., The Treatment of Chronic back Pain: A Preliminary survey of the Effect of Radiofrequency Denervation of the Posterior Vertebral Joints, vol. 34 (1979) pp. 768-775.
Patil et al., Percutaneous Discectomy Using the Electomagnetc Field Focusing Probe: A Feasability Study.
McCulloch et al., CMA Journal: Percutaneous Radiofrequency Lumbar Rhizolysis (rhizotomy), vol. 116, Jan. 8, 1977.

Yonezawa et al., The System and Procedure of Percutaneous Intradiscal Laser Nucleotomy, vol. 15 No. 11 (1990).
Sminia et al., Effects of 434 MHz Microwave Hyperthermia applied to the rat in the region of the cervical Spinal Cord, vol. 3 No. 5 (1987) pp. 441-452.
Sluijter et al., Treatment of Chronic Back and Neck Pain by Percutaneous Therman Lesions, vol. 3 (1981).
Auhll, Richard A., "The Use of the Resectoscope in Gynecology." Biomedical Business International, Oct. 11, 1990, pp. 91-93.
Christian, C. et al., "Allograft Anterior Cruciate Ligament Reconstruction with Patellar Tendon: An Endoscopic Technique", Operative Techniques in Sports Medicine, vol. 1, No. 1, Jan. 1993, pp. 50-57.
Houpt, J. et al., "Experimental Study of Temperature Distributions and Thermal Transport During Radiofrequency Current Therapy of the Intervertebral Disc", Spine, vol. 21, No. 15, (1996), pp. 1808-1813.
Troussier, B. et al., "Percutaneous Intradiscal Radio-Frequency Thermocoagulation: A Cadaveric Study", Spine, vol. 20, No. 15, (Aug. 1995), pp. 1713-1718.
Beadling, L., "Bi-Polar electrosurgical devices: Sculpting the future of arthroscopy", Orthopedics today, vol. 17, No. 1, Jan. 1997, 4 pages.
Ellman International Mfg., Inc., 1989, Catalog, pp. 1-15, 20.
Cosset, J.M., Resistive Radiofrequency (Low Frequency) Intertitial Heating (RF Technique), Interstitial Hyperthermia, Dec. 6, 1993, pp. 3-5, 37.
Attachment I: Competitive Literature on Generators with Bipolar Capabilities, IME Co., Ltd., pp. 60-86.
Attachment II: Competitive Literature on Bipolar Forceps and Footswitch Controls, IME Co., Ltd. pp. 87-104.
Gerber et al., Der Orthopade: Offene Laserchirurgie am Bewegungsapparat, vol. 25, (1996) pp. 56-63.
Vorwerck et al., Laserablation des Nucleus Pulposus: Optische Eigenschaften von Degeneriertem Bandscheibengewebe im Wellenlangenbereich von 200 bis 2200 nm, vol. 151 No. 6, (1989) pp. 725-728.
"Answer and Counterclaim of Defendant Tyco Healthcare Group LP in Civil Action No. 01-558" (U.S. District Court, District of Columbia).
Answer and Counterclaims of Defendant Arthrocare Corporation, filed Aug. 7, 2003, in re Smith & Nephew, Inc. v. Arthrocare Corporation (No. 03-2214 MaA, USDC, Western District of Tennessee, Western Division.
Fine, B.S., and Yanoff, Y., Ocular Histology, 2$^{nd}$ Ed., pp. 130-159, Harper & Row, Hagerstown, Maryland, 1979.
Cosman, E.R., and Cosman, B.J., "Methods of Making Nervous System Lesions," Neurosurgery, R.H. Wilkins and S.S. Rengachary, eds., Chapter 337, pp. 2490-2499.
Elsasser et al., "An instrument for transurethral resection without leakage of current," Medizinal-Markt/Acta Medicotechnica, vol. 24 (4), 1976 129-134.
"Lase®... The Next Step in Conservative Therapy for Patients with Contained Herniated Discs," Clarus Medical, reprinted from http://www.clarus-medical.com/lase.htm, 5 pages.
"LASE Patient Information", Clarus medical, reprinted from http://www.clarus-medical.com/lase.htm, 5 pages.
Tobler et al., "Improved Outcome in the Treatment of Trigeminal Neuralgia by Percutaneous Stereostatic Rhizotomy with a New, Curved Tip Electrode," Neurosurgery, 12 (3), 1983, 313-317.
Zinn, K.M. and Mockel-Pohl, S., "The Lens and Zonules," Ocular Fine Structure for the Clinician, vol. 13, No. 3, 1973, pp. 143-155.
Surgical Dynamics, "Discography System For Contemporary Spine Surgery," copyright 1991 (2 pages).
Surgical Dynamics, "Nucleotome System Automated Percutaneous Lumbar Discectomy" (3 pages).
Surgical Dynamics, "Nucleotome Flex II For Automated Percutaneous Lumbar Discectomy," copyright 1992 (2 pages).
Surgical Dynamics, "Surgical Technique Nucleotome Flex II for Automated Percutaneous Lumbar Discectomy," copyright 1992 (21 pages).
Surgical Dynamics, "Nucleotome Micro I For Automated Open Lumbar Discectomy," copyright 1992 (2 pages).

Surgical Dynamics, "Surgical Technique Nucleotome Micro I for Automated Open Lumbar Discectomy," copyright 1992 (4 pages).
Bernhardt, et al., "Magnetic Resonance Imaging Analysis of Percutaneous Discectomy: A Preliminary Report," *Spine*, 18(2):211-217 (Feb 1993).
Capanna, A. et al., "Lumbar Discectomy-Percentage of disc removal and detection of anterior annulus performation," *Spine*, 6(6): 610-614 (Nov./Dec. 1981).
Castro, et al., "Restriction of Indication for Automated Percutaneous Lumbar Discectomy Based on Computed Tomographic Discography," *Spine*, 17(10):1239-1243 (Oct. 1992).
Cooney, "Percutaneous Lumbar Discectomy," *Clinics in Sports Medicine*, 12(3):557-568 (Jul. 1993).
Davis, G.W.et al., "Automated Percutaneous Discetomy," *Spine*, 16(3):359-363, (Mar. 1991).
Day, P.L., "Lateral Approach For Lumbar Diskogram And Chemonucleloysis," *Clinical Orthopaedics and Related Research*, No. 67 (Nov./Dec. 1969).
Garvin, P., et al., "Chymopapain: A Pharmacologic And Toxicologic Evaluation In Experimental Animals," Meeting of the Chicago Orthopedic Society, pp. 204-223 (May 10, 1963).
Gunzburg, et al., "An Experimental Study Comparing Percutaneous Discectomy with Chemonucleolysis," *Spine*, 18(2):218-226 (Feb. 1993).
Jacobson, "Lumbar Percutaneous Diskectomy," *Bulletin of the Hospital for Joint Diseases Orthopaedic Instiute*, vol. 48, No. 1 (1988).
Kahanovitz, et al., "A Multicenter Analysis of Percutaneous Discectomy," *Spine*, 15(7):713-715 (Jul. 1990).
Kambin, et al., "Arthroscopic Microdiscetomy versus Nucleotomy Techniques," *Clinics in Sports Medicine*, 12(3):587-598 (Jul. 1993).
Kambin, et al., "Development of Degenerative Spondylosis of the Lumbar Spine After Partial Discectomy," *Spine*, 20(5):599-607 (Mar. 1, 1995).
Kambin, et al., "History and Current Status of Percutaneous Arthroscopic Disc Surgery," *Spine*, 21(245):575-615 (Dec. 15, 1996).
Kambin, et al., "Percutaneous Posterolateral Discectomy: Anatomy and Mechanism," *Clinical Orthopaedics and Related Research*, No. 223 (Oct. 1987).
Kaufman, H. et al., "Mechanical Aspiration Of Hematomas In An In Vitro Model," *Neurosurgery*, 25(3):347-350 (Sep. 1989).
Kornberg, "Automated Percutaneous Lumbar Discectomy as Treatment for Lumbar Disc Disruption," *Spine*, 18(3):395-397 (Mar. 1993).
Koutrouvelis, et al., "Stereotactic Percutaneous Lumbar Discectomy," *Neurosurgery*, 32(4):582-586 (Apr. 1993).
Liebler, "Percutaneous Laser Disc Decompression: Clinical Experience with the Nd:YAG and KTP Lasers," *Spine: State of the Art Reviews*, 7(1):55-65 (Jan. 1993).
Lorenz, M. et al., "Chemonucleolysis for Hernated Nucleous Pulposus In Adolescents," *Journal of Bone and Joint Surgery*, 67-A(9): 1402-1404 (Dec. 1985).
Maroon, J. et al., "Percutaneous Automate Discectomy: A New Method For Lumbar Disc Removal, Technical Note," *Journal of Neurosurgery*, 66(1): 143-146 (Jan. 1987).
Maroon, J. et al., "Percutaneous Automated Discectomy, A New Approach To Lumbar Surgery," *Clinical Orthopaedics and Related Research*, No. 238, pp. 64-70 (Jan. 1989).
Maroon, et al., "Percutaneous Discectomy for Lumbar Disc Herniation," *Neurosurgery Clinics of North America*, 4(1):125-134 (Jan. 1993).
Mayer, et al., "Percutaneous Endoscopic Laser Discectomy (PELD): A New Surgical Technique for Non-sequestrated Lumbar Discs," *Acta Neurochirurgica*, Supp 54, pp. 53-58 (1992).
Mayer, "Spine Update: Percutaneous Lumbar Disc Surgery," *Spine*, 19(23):2719-2723, (Dec. 1994).
Mochida, et al., "Percutaneous Nucleotomy in Lumbar Disc Herniation: A Prospective Study," *Spine*, 18(14):2063-2068 (Oct. 15, 1993).
O'Laoire, S., et al., "Spinal Cord Compression Due to Prolapse Of Cerival Intervertebral Disc (Herniation Of Nucleus Pulposus)," *Journal of Neurosurgery*, 59, pp. 847-853 (1983).
Onik, G., et al., "Percutaneous Lumbar Diskectomy Using A New Aspiration Probe: Porcine And Cadaver Model," *Radiology*, 155(1):251-252 (Apr. 1985).
Onik, G., et al., "Percutaneous Lumbar Diskectomy Using A New Aspiration Probe: Preliminary Results," [Journal of clinical and laboratory research,] *Investigative Radiology*, 20(6):S18 (Sep. 1985).
Onik, G., et al., "Percutaneous Lumbar Diskectomy Using A New Aspiration Probe," *American Journal of Roentgenology*, 144:1137-1140 (Jun. 1985).
Onik, G., et al., "Automated Percutaneous Diskectomy: Initial Patient Experience Work In Progress," *Radiology*, 162(1): 129-132 (Jan. 1987).
Onik, G., et al., "Automated Percutaneous Discectomy at the L5-S1 Level: Use of a Curved Cannula," *Clinical Orthopaedics and Related Research*, No. 238, pp. 71-76 (Jan. 1989).
Onik, G., et al., "Automated Percutaneous Discectomy: A Prospective Multi-Institutional Study," *Neurosurgery*, 26(2):228-233 (Feb. 1990).
Patsiaouras, et al., "Percutaneous Nucleotomy: An Anatomic Study of the Risks of Root Injury," *Spine*, 16(1):39-42 (Jan. 1991).
Plancarte et al., "Complex Regional Pain Syndrome Type 2 (Causalgia) After Automated Laser Discetomy: A Case Report," *Spine*, 22(4):459-462, (Feb. 15, 1997).
Quigley, et al., "Laser Discectomy: A Review," *Spine* 19(1):53-56 (Jan. 1, 1993).
Quigley, et al., "Percutaneous Laser Discectomy with the Ho:YAG Laser," *Lasers in Surgery and Medicine*, 12(6):621-624 (1992).
Revel, et al., "Automated Percutaneous Lumbar Discectomy Versus Chemonucleolysis in the Treatment of Sciatica: A Randomized Multicenter Trial," *Spine*, 18(1):1-7 (Jan. 1993).
Shevlin, W. et al., "Perforation of the Anterior Annulus During Lumbar Discectomy," *Journal of Neurosurgery*, vol. 38, No. 4, pp. 514-515 (Apr. 1973).
Sluijter, et al., "Letter To The Editor," *Spine*, 21(4):528-529 (Feb. 15, 1996).
Smith, L. et al., "Enzyme Dissolution Of The Nucleous Pulposus," *Nature*, vol. 198, pp. 1311-1312 (1963).
Smith, L. et al., "Enzyme Dissolution Of The Nucleous Pulposus In Humans," *JAMA*, 187(2):177-180 (Jan. 1964).
Smith, L. et al., "Treatment of Lumbar Intervertebral Disc Lesions By Direct Injection Of Chymopapain," *Journal of Bone and Joint Surgery*, 49B(3): 502-519 (Aug. 1967).
Sussman, B., "Intervertebral Discolysis With Collagenase," *Journal of the National Medical Association*, 60(3): 184-187 (May 1968).
Sussman, B. et al., "Experimental Intervertebral Discolysis With Collagenase," *Journal of Neurosurgery*, 31: 628-635 (Dec. 1969).
Sussman, B., "Inadequacies and Hazards Of Chymopapain Injections As Treatment For Inteverterbral Disc Disease," *Journal of Neurosurgery*, 42: 389-396 (Apr. 1975).
Ulrich, "Automatisierte perkutane Nukleotomie," *Zeitschrift fur Orthopaedie und Ihre Grenzbebiete*, No. 130, pp. 45-50 (Jan./Feb. 1992).
van Kleef, M., et al., "Percutaneous Intradiscal Radio-Frequency Thermocoagulation In Chronic Non-Specific Low Back-Pain," *The Pain Clinic*, 9(3):259-268 (1996).
Williams, R., "Microlumbar Discectomy, A Conservative Surgical Approach To The Virgin Herniated Lumbar Disc," *Spine*, 3(2): 175-182 (Jun. 1978).
Yeo, et al., "Clinical Experience with Automated Percutaneous Discectomy," *Singapore Medical Journal*, 34(4):313-315 (Aug. 1993).
Yeung, A., "Considerations for Use of the KTP Laser for Disc Decompression and Ablation," *Spine: State of the Art Reviews*, 7(1): 67-93 (Jan. 1993).
Yeung, A., "The evolution of Percutaneous Spinal Endoscopy And Discectomy: State Of The Art," *The Mount Sinai Journal of Medicine*, 67(4): 327-332 (Sep. 2000).
Zhou, et al., "Percutaneous Lumbar Discectomy Using a New Nucleotome System: Report of 182 Cases," *Chinese Medical Journal*, 106(6):446-451 (Jun. 1993).

"ArthroCare's Opening *Markman* Brief Regarding U.S. Patent Nos. 5,980,504 and 6,261,311," filed in U.S. District Court for the Western District of Tennessee Western Division on Feb. 20, 2004, 31 pages.

"Smith & Nephew's Opening Markman Brief for U.S. Patent Nos. 5,980,504 and 6,261,311," filed in U.S. District Court for the Western District of Tennessee Western Division on Feb. 20, 2004, 23 pages.

"ArthroCare Corporation's Brief in Opposition to Smith & Nephew's Opening Markman Brief for U.S. Patent Nos. 5,980,504 and 6,261,311," filed in U.S. District Court for the Western District of Tennessee Western Division on Mar. 26, 2004, 21 pages.

"Smith & Nephew Inc.'s Opposition Markman Brief for U.S. Patent Nos. 5,980,504 and 6,261,311," filed in U.S. District Court for the Western District of Tennessee Western Division on Mar. 26, 2004, 44 pages.

US 6,645,204, 11/2003, Sharkey et al. (withdrawn)

US 6,648,884, 11/2003, To et al. (withdrawn)

* cited by examiner ns are incorporated herein by reference in tbeir entirety.

METHOD FOR TREATING INTERVERTEBRAL DISCS

CROSS-REFERENCE TO RELATED APPLICATIONS

This application is a continuation of U.S. patent application Ser. No. 10/388,609, filed Mar. 17, 2003, now U.S. Pat. No. 6,997,941, which is a continuation of U.S. patent application Ser. No. 09/707,627, filed, Nov. 6, 2000, now U.S. Pat. No. 6,547,810, which is a continuation of U.S. application Ser. No. 09/236,816, flied Jan. 25, 1999, now U.S. Pat. No. 6,290,715, which is a continuation of (i) U.S. application Ser. No. 09/162,704 filed Sep. 29, 1998, now U.S. Pat. No. 6,099,514, (ii) U.S. patent application Ser. No. 09/153,552 filed Sep. 15, 1998, now U.S. Pat. No. 6,126, 682, and (iii) U.S. patent application Ser. No. 08/881,525 now U.S. Pat. No. 6,122,549, U.S. patent application Ser. No. 08/881,692, now U.S. Pat. No. 6,073,051, U.S. patent application Ser. No. 08/881,527, now U.S. Pat. No. 5,980, 504, U.S. patent application Ser. No. 08/881,693, now U.S. Pat. No. 6,007,570, and U.S. patent application Ser. No. 08/881,694, now U.S. Pat. No. 6,095,149, each filed Jun. 24, 1997, claiming priority from provisional application Nos. 60/047,820, 60/047,841, 60/047,818 and 60/047,848, each filed May 28, 1997, provisional application No. 60/045,941, filed May 8, 1997, and provisional application Nos. 60/029, 734, 60/029,735, 60/029,600, and 60/029,602, each filed Oct. 23, 1996. This application is a continuation-in-part of U.S. patent application Ser. No. 09/876,833, now U.S. Pat. No. 6,726,685, Ser. No. 09/876,832, now U.S. Pat. No. 6,733,496 and Ser. No. 09/876,831, now U.S. Pat. No. 6,832,997 each filed June 6, 2001. This application is a continuation-in-part of U.S. patent application Ser. No. 10/624,894, filed Jul. 23, 2003, now abandoned which is a divisional of U.S. patent application Ser. No. 09/753,786, filed Jan. 2, 2001, now U.S. Pat. No. 6,645,203, which is a continuation-in-part of U.S. patent application Ser. No. 09/022,688, filed Feb. 12, 1998, now U.S. Pat. No. 6,168, 593, which claims priority from provisional application No. 60/037,620, filed Feb. 12, 1997. This application is a continuation-in-part of U.S. patent application Ser. No. 10/242, 077, filed Sep. 13, 2002, now abandoned which is a divisional of U.S. patent application Ser. No. 09/340,065, filed Jun. 25, 1999, now U.S. Pat. No. 6,461,357, which is a continuation-in-part of U.S. patent application Ser. No. 09/022,612, filed Feb. 12, 1998, now U.S. Pat. No. 6,135, 999, which claims priority from provisional application No. 60/037,782, filed Feb. 12, 1997. This application is a continuation-in-part of U.S. patent application Ser. No. 09/776, 231, now U.S. Pat. No. 6,767,347 and Ser. No. 09/776,186, now U.S. Pat. No. 6,749,605, both filed Feb. 1, 2001, both of which are divisionals of U.S. patent application Ser. No. 09/272,806, filed Mar. 19, 1999, now U.S. Pat. No. 6,258, 086, which claims priority from provisional application No. 60/078,545, filed Mar. 19, 1998. This application is a continuation-in-part of U.S. patent application Ser. No. 09/884,859, filed Jun. 18, 2001, now U.S. Pat. No. 6,878, 155, which is a continuation of U.S. patent application Ser. No. 09/792,628 filed Feb. 22, 2001, now U.S. Pat. No. 7,069,087, which claims priority from provisional application No. 60/185,221, filed Feb. 25, 2000. This application is a continuation-in-part of U.S. patent application Ser. No. 09/664,473, filed Sep. 18, 2000, which is a continuation of U.S. patent application Ser. No. 08/696,051, filed Aug. 13, 1996, now abandoned. All of the above-mentioned applications are incorporated herein by reference in tbeir entirety.

TECHNICAL FIELD

This document relates to methods and apparatuses for modifying intervertebral disc tissue and more particularly to the treatment of annular fissures and other conditions using percutaneous techniques to avoid major surgical intervention.

BACKGROUND

Intervertebral disc abnormalities have a high incidence in the population and may result in pain and discomfort if they impinge on or irritate nerves. Disc abnormalities may be the result of trauma, repetitive use, metabolic disorders and the aging process and include such disorders but are not limited to degenerative discs (i) localized tears or fissures in the annulus fibrosus, (ii) localized disc herniations with contained or escaped extrusions, and (iii) chronic, circumferential bulging disc.

Disc fissures occur rather easily after structural degeneration (a part of the aging process that may be accelerated by trauma) of fibrous components of the annulus fibrosus. Sneezing, bending or just attrition can tear these degenerated annulus fibers, creating a fissure. The fissure may or may not be accompanied by extrusion of nucleus pulposus material into or beyond the annulus fibrosus. The fissure itself may be the sole morphological change, above and beyond generalized degenerative changes in the connective tissue of the disc. Even if there is no visible extrusion, biochemicals within the disc may still irritate surrounding structures. Disc fissures can be debilitatingly painful. Initial treatment is symptomatic, including bed rest, painkillers and muscle relaxants. More recently spinal fusion with cages have been performed when conservative treatment did not relieve the pain. The fissure may also be associated with a herniation of that portion of the annulus.

With a contained disc herniation, there are no free nucleus fragments in the spinal canal. Nevertheless, even a contained disc herniation is problematic because the outward protrusion can press on the spinal nerves or irritate other structures. In addition to nerve root compression, escaped nucleus pulposus contents may chemically irritate neural structures. Current treatment methods include reduction of pressure on the annulus by removing some of the interior nucleus pulposus material by percutaneous nuclectomy. However, complications include disc space infection, nerve root injury, hematoma formation, instability of the adjacent vertebrae and collapse of the disc from decrease in height.

Another disc problem occurs when the disc bulges outward circumferentially in all directions and not just in one location. Over time, the disc weakens and takes on a "roll" shape or circumferential bulge. Mechanical stiffness of the joint is reduced and the joint may become unstable. One vertebra may settle on top of another. This problem continues as the body ages and accounts for shortened stature in old age. With the increasing life expectancy of the population, such degenerative disc disease and impairment of nerve function are becoming major public health problems. As the disc "roll" extends beyond the normal circumference, the disc height may be compromised, foramina with nerve roots are compressed. In addition, osteophytes may form on the outer surface of the disc roll and further encroach on the spinal canal and foramina through which nerves pass. This condition is called lumbar spondylosis.

It has been thought that such disc degeneration creates segmental instability which disturbs sensitive structures which in turn register pain. Traditional, conservative methods of treatment include bed rest, pain medication, physical therapy or steroid injection. Upon failure of conservative therapy, spinal pain (assumed to be due to instability) has been treated by spinal fusion, with or without instrumentation, which causes the vertebrae above and below the disc to grow solidly together and form a single, solid piece of bone. The procedure is carried out with or without discectomy. Other treatments include discectomy alone or disc decompression with or without fusion. Nuclectomy can be performed by removing some of the nucleus to reduce pressure on the annulus. However, complications include disc space infection, nerve root injury, hematoma formation, and instability of adjacent vertebrae.

These interventions have been problematic in that alleviation of back pain is unpredictable even if surgery appears successful. In attempts to overcome these difficulties, new fixation devices have been introduced to the market, including but not limited to pedicle screws and interbody fusion cages. Although pedicle screws provide a high fusion success rate, there is still no direct correlation between fusion success and patient improvement in function and pain. Studies on fusion have demonstrated success rates of between 50% and 67% for pain improvement, and a significant number of patients have more pain postoperatively. Therefore, different methods of helping patients with degenerative disc problems need to be explored.

FIGS. 1(a) and 1(b) illustrate a cross-sectional anatomical view of a vertebra and associated disc and a lateral view of a portion of a lumbar and thoracic spine, respectively. Structures of a typical cervical vertebra (superior aspect) are shown in FIG. 1(a): 104—lamina: 106—spinal cord: 108—dorsal root of spinal nerve; 114—ventral root of spinal nerve; 116—posterior longitudinal ligament: 118—intervertebral disc; 120—nucleus pulposus; 122—annulus fibrosus; 124—anterior longitudinal ligament; 126—vertebral body; 128—pedicle; 130—vertebral artery; 132—vertebral veins; 134—superior articular facet; 136—posterior lateral portion of the annulus; 138—posterior medial portion of the annulus; and 142—spinous process. In FIG. 1(a), one side of the intervertebral disc 118 is not shown so that the anterior vertebral body 126 can be seen. FIG. 1(b) is a lateral aspect of the lower portion of a typical spinal column showing the entire lumbar region and part of the thoracic region and displaying the following structures: 118—intervertebral disc; 126—vertebral body; 142—spinous process; 170—inferior vertebral notch; 110—spinal nerve; 174—superior articular process; 176—lumbar curvature; and 180—sacrum.

The presence of the spinal cord and the posterior portion of the vertebral body, including the spinous process, and superior and inferior articular processes, prohibit introduction of a needle or trocar from a directly posterior position. This is important because the posterior disc wall is the site of symptomatic annulus tears and disc protrusions/extrusions that compress or irritate spinal nerves for most degenerative disc syndromes. The inferior articular process, along with the pedicle and the lumbar spinal nerve, form a small "triangular" window (shown in black in FIG. 1(c)) through which introduction can be achieved from the posterior lateral approach. FIG. 1(d) looks down on an instrument introduced by the posterior lateral approach. It is well known to those skilled in the art that percutaneous access to the disc is achieved by placing an introducer into the disc from this posterior lateral approach, but the triangular window does not allow much room to maneuver. Once the introducer pierces the tough annulus fibrosus, the introducer is fixed at two points along its length and has very little freedom of movement. Thus, this approach has allowed access only to small central and anterior portions of the nucleus pulposus. Current methods do not permit percutaneous access to the posterior half of the nucleus or to the posterior wall of the disc. Major and potentially dangerous surgery is required to access these areas.

U.S. Pat. No. 5,433,739 (the "'739 patent") discloses placement of an RF electrode in an interior region of the disc approximately at the center of the disc. RF power is applied, and heat then putatively spreads out globally throughout the disc. The '739 patent teaches the use of a rigid shaft which includes a sharpened distal end that penetrates through the annulus fibrosus and into the nucleus pulposus. In one embodiment the shaft has to be rigid enough to permit the distal end of the RF electrode to pierce the annulus fibrosus, and the ability to maneuver its distal end within the nucleus pulposus is limited. In another embodiment, a somewhat more flexible shaft is disclosed. However, neither embodiment of the devices of the '739 patent permits access to the posterior, posterior lateral and posterior medial region of the disc, nor do they provide for focal delivery of therapy to a selected local region within the disc or precise temperature control at the annulus. The '739 patent teaches the relief of pain by globally heating the disc. There is no disclosure of treating an annular tear or fissure.

U.S. Pat. No. 5,201,729 (the "'729 patent") discloses the use of an optical fiber that is introduced into a nucleus pulposus. In the '729 patent, the distal end of a stiff optical fiber shaft extends in a lateral direction relative to a longitudinal axis of an introducer. This prevents delivery of coherent energy into the nucleus pulposus in the direction of the longitudinal axis of the introducer. Due to the constrained access from the posterior lateral approach, stiff shaft and lateral energy delivery, the device of the '729 patent is unable to gain close proximity to selected portion(s) of the annulus (i.e., posterior, posterior medial and central posterior) requiring treatment or to precisely control the temperature at the annulus. No use in treating an annular fissure is disclosed. The device of the '729 patent describes ablating the nucleus pulposus.

Accordingly, it is desirable to diagnose and treat disc abnormalities at locations previously not accessible via percutaneous approaches and without substantial destruction to the disc. It would further be desirable to be able to administer materials to a precise, selected location within the disc, particularly to the location of the annular fissure. It would be further desirable to provide thermal energy into collagen in the area of the fissure to strengthen the annulus and possibly fuse collagen to the sides of the fissure, particularly at the posterior, posterior lateral and the posterior medial regions of the inner wall of the annulus fibrosus.

SUMMARY

Accordingly, one aspect of the invention features a minimally invasive method and apparatus for diagnosing and treating fissures of discs at selected locations within the disc.

Another aspect features an apparatus which is advanceable and navigable at the inner wall of the annulus fibrosus to provide localized heating at the site of the annular fissure.

Another aspect features a method and apparatus to treat degenerative intervertebral discs by delivering thermal energy to at least a portion of the nucleus pulposus to reduce water content of the nucleus pulposus and shrink the nucleus pulposus.

Still a further aspect features a device which has a distal end that is inserted into the disc and accesses the posterior, posterior lateral and the posterior medial regions of the inner wall of the annulus fibrosus in order to repair or shrink an annular fissure at such a location.

Methods for manipulating a disc tissue with a fissure or tear in an intervertebral disc, the disc having a nucleus pulposus and an annulus fibrosus, the annulus having an inner wall of the annulus fibrosus, employ an externally guidable intervertebral disc apparatus, or catheter. The procedure is performed with a catheter having a distal end, a proximal end, a longitudinal axis, and an intradiscal section at the catheter's distal end on which there is at least one functional element. The catheter is advanced through the nucleus pulposus and around an inner wall of an annulus fibrosus by applying a force to the proximal end but the applied force is insufficient for the intradiscal section to puncture the annulus fibrosus. The next step is positioning the functional element at a selected location of the disc by advancing or retracting the catheter and optionally twisting the proximal end of the catheter. Then the functional unit treats the annular fissure.

A method of treating an intervertebral fissure includes placing an energy source adjacent to the fissure and providing sufficient energy to the fissure to raise the temperature to at least about 45-70° C. and for a sufficient time to cause the collagen to weld.

Yet another method of treating an intervertebral fissure includes placing a catheter with a lumen adjacent to the fissure and injecting sealant into the fissure via the catheter lumen to seal the fissure.

In addition to the methods, there is provided an externally guidable intervertebral disc apparatus for diagnosis or manipulation of disc tissue present at a selected location of an intervertebral disc, the disc having a nucleus pulposus, an annulus fibrosus, and an inner wall of the annulus fibrosus, the nucleus pulposus having a diameter in a disc plane between opposing sections of the inner wall. The apparatus comprises a catheter having a distal end, a proximal end, and a longitudinal axis, and an intradiscal section at the catheter's distal end, which is extendible into the disc, has sufficient rigidity to be advanceable through the nucleus pulposus and around the inner wall of the annulus fibrosus under a force applied longitudinally to the proximal end, has sufficient flexibility in a direction of the disc plane to be compliant with the inner wall, and has insufficient penetration ability to be advanceable out through the annulus fibrosus under the force; and a functional element located at the intradiscal section for adding sufficient thermal energy at or near the fissure.

According to another aspect of the invention, an intervertebral disc apparatus includes an introducer and a catheter. The introducer includes an introducer lumen. The catheter is at least partially positionable in the introducer lumen. The catheter includes an intradiscal section and an energy delivery device coupled to the intradiscal section. The intradiscal section is configured to be advanceable through a nucleus pulposus of the intervertebral disc and positionable adjacent to a selected site of an inner wall of an annulus fibrosus. Embodiments of this aspect may include that the energy delivery device is configured to deliver sufficient energy to, e.g., create a selected ablation of a selected site of the intervertebral disc, reduce an intradiscal pressure of the intervertebral disc, and/or provide a denervation of a nerve at a selected site of the intervertebral disc. The energy delivery device includes, e.g., an RF electrode configured to be coupled to an RF energy source.

According to another aspect of the invention, a method of treating back or neck pain includes providing a catheter deployable from an introducer lumen, the catheter including an intradiscal section coupled to an energy delivery device, wherein the intradiscal section is advanceable through a nucleus pulposus and positionable along a selected site of an inner wall of an annulus fibrosus. The method includes advancing the intradiscal section into the nucleus pulposus from a distal end of the introducer lumen and positioning at least a portion of the intradiscal section along at least a portion of the inner wall of the annulus fibrosus to the selected site. Embodiments of this aspect may include delivering sufficient energy from the energy delivery device to, e.g., create a selected ablation of a selected site of the intervertebral disc, reduce an intradiscal pressure of the intervertebral disc and/or denervate a nerve of the intervertebral disc.

Another aspect features an intervertebral disc apparatus including a catheter at least partially positionable in an introducer lumen. The catheter includes an intradiscal section and an energy delivery device coupled to the intradiscal section. The intradiscal section is configured to be advanceable through a nucleus pulposus of the intervertebral disc and navigationable along an inner wall of an annulus fibrosus. Embodiments of this aspect of the invention may include multiple electrodes that operate in a bipolar mode.

The details of one or more embodiments are set forth in the drawings and the description below. Other features will be apparent from the description and drawings, and from the claims.

DETAILED DESCRIPTION

Figure 1A:
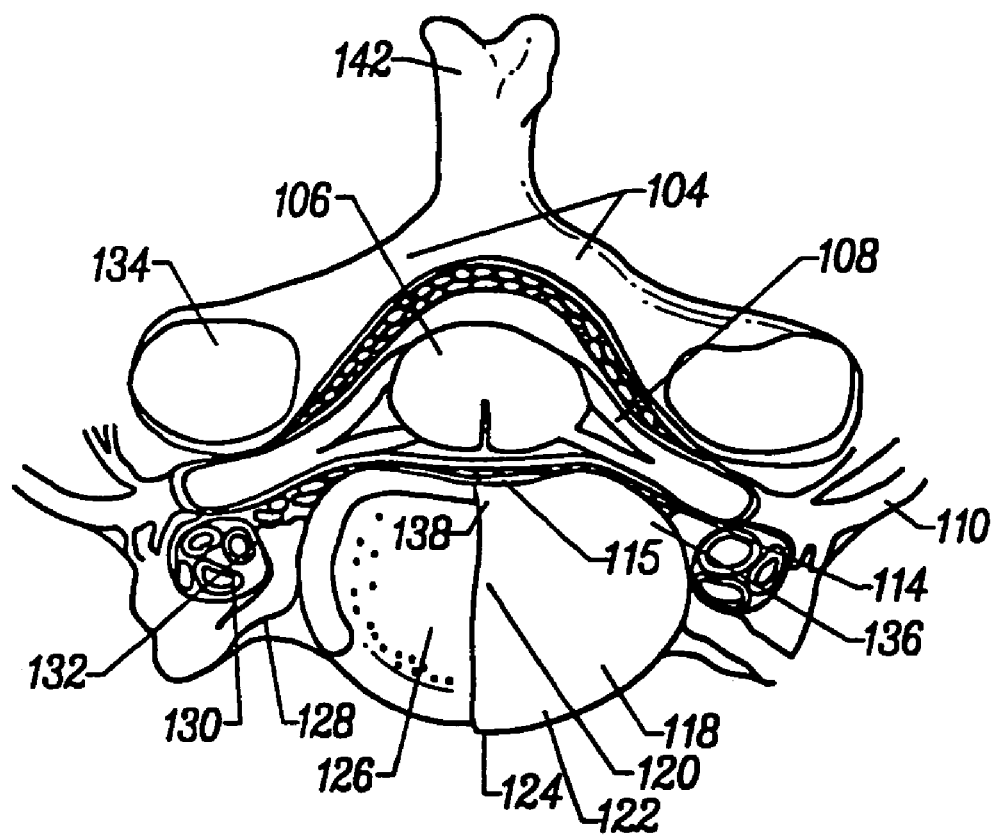
FIG. 1(a) is a superior cross-sectional anatomical view of a cervical disc and vertebra.
Figure 1B:
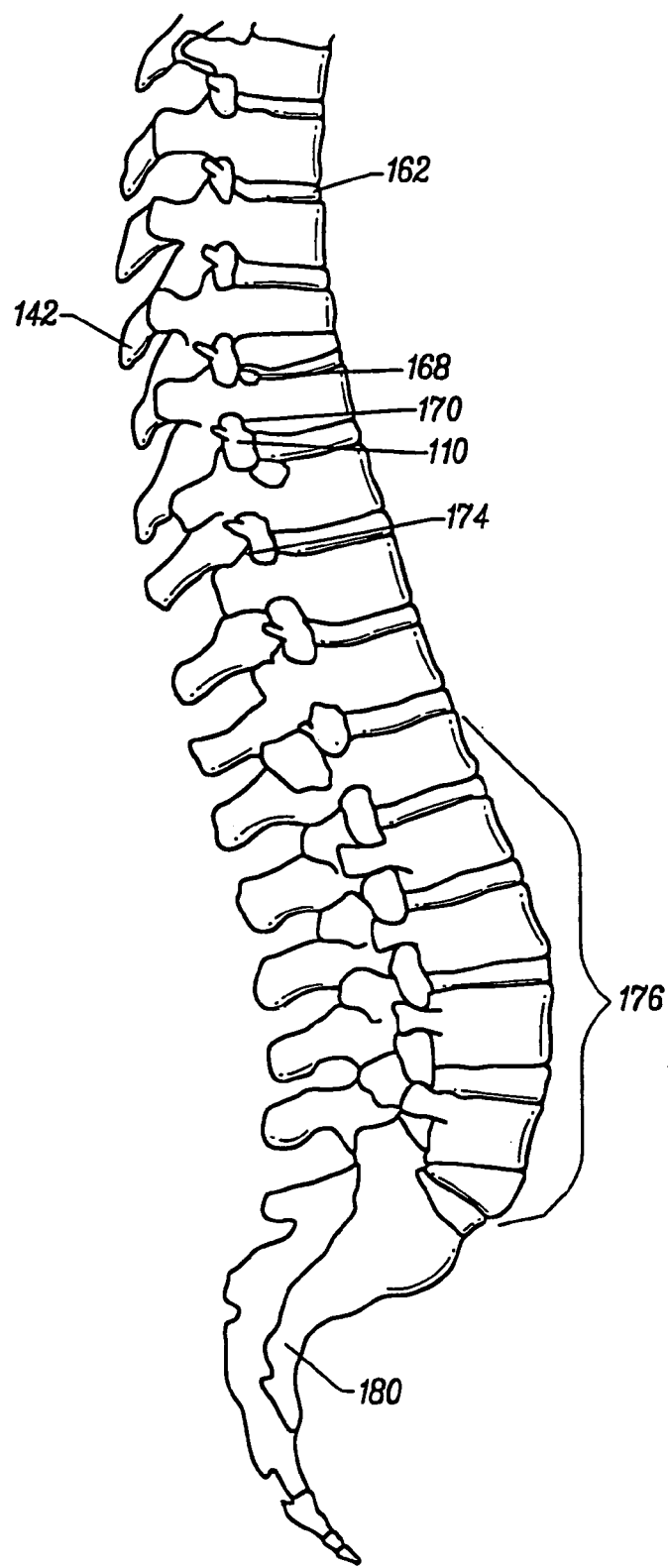
FIG. 1(b) is a lateral anatomical view of a portion of a lumbar spine.
Figure 1D:
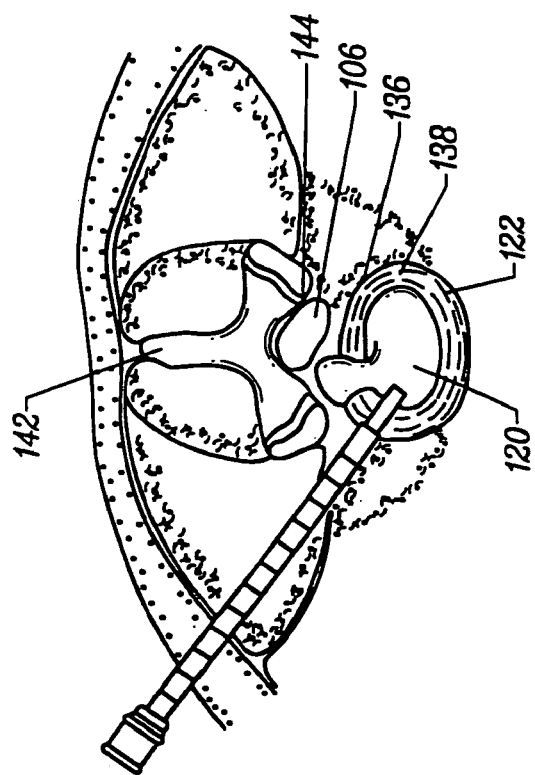
FIG. 1(d) is a superior cross-sectional view of the required posterior lateral approach.
Figure 1C:
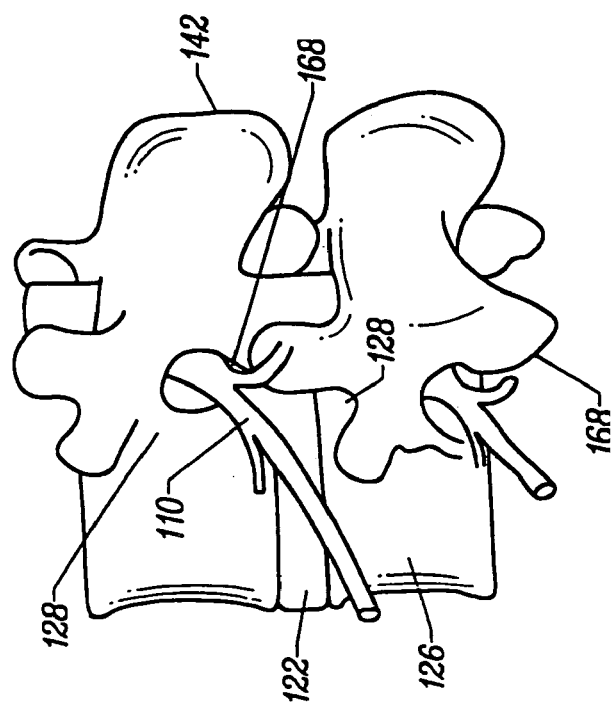
FIG. 1(c) is a posterior-lateral anatomical view of two lumbar vertebrae and illustration of the triangular working zone.

The present invention provides a method and apparatus for diagnosing and treating intervertebral disc disorders, such as, for example, tears of fissures of the annulus fibrosus, herniations, and circumferential bulging, which may or may not be accompanied with contained or escaped extrusions.

In general, an apparatus of the invention is in the form of an externally guidable intervertebral disc apparatus for accessing and manipulating disc tissue present at a selected location of an intervertebral disc having a nucleus pulposus and an annulus fibrosus, the annulus having an inner wall. Use of a temperature-controlled energy delivery element, combined with the navigational control of the inventive catheter, provides preferential, localized heating to treat the fissure. For ease of reference to various manipulations and distances described below, the nucleus pulposus can be considered as having a given diameter in a disc plane between opposing sections of the inner wall. This nucleus pulposus diameter measurement allows instrument sizes (and parts of instruments) designed for one size disc to be readily converted to sizes suitable for an instrument designed for a different size of disc.

The operational portion of the apparatus of the invention is brought to a location in or near the disc's fissure using techniques and apparatuses typical of percutaneous interventions. For convenience and to indicate that the apparatus of the invention can be used with any insertional apparatus that provides proximity to the disc, including many such insertional apparatuses known in the art, the term "introducer" is used to describe this aid to the method. An introducer has an internal introducer lumen with a distal opening at a terminus of the introducer to allow insertion (and manipulation) of the operational parts of the apparatus into (and in) the interior of a disc.

The operational part of the apparatus comprises an elongated element referred to as a catheter, various parts of which are located by reference to a distal end and a proximal end at opposite ends of its longitudinal axis. The proximal end is the end closest to the external environment surrounding the body being operated upon (which may still be inside the body in some embodiments if the catheter is attached to a handle insertable into the introducer). The distal end of the catheter is intended to be located inside the disc under conditions of use. The catheter is not necessarily a traditional medical catheter (i.e., an elongate hollow tube for admission or removal of fluids from an internal body cavity) but is a defined term for the purposes of this specification. "Catheter" has been selected as the operant word to describe this part of the apparatus, as the inventive apparatus is a long, flexible tube which transmits energy and/or material from a location external to the body to a location internal to the disc being accessed upon, such as a collagen solution and heat to the annular fissure. Alternatively, material can be transported in the other direction to remove material from the disc, such as removing material by aspiration to decrease pressure which is keeping the fissure open and aggravating the symptoms due to the fissure. Material may be removed to decrease intradiscal pressure which maintains a herniation.

The catheter is adapted to slidably advance through the introducer lumen, the catheter having an intradiscal section at the distal end of the catheter, the intradiscal section being extendible through the distal opening at the terminus of the introducer into the disc. Although the length of the intradiscal portion can vary with the intended function as explained in detail below, a typical distance of extension is at least one-half the diameter of the nucleus pulposus, preferably in the range of one-half to one and one-half times the circumference of the nucleus pulposus. In order that the functional elements of the catheter can be readily guided to the desired location within a disc, the intradiscal portion of the catheter is manufactured with sufficient rigidity to avoid collapsing upon itself while being advanced through the nucleus pulposus and navigated around the inner wall of the annulus fibrosus. The intradiscal portion, however, has insufficient rigidity to puncture the annulus fibrosus under the same force used to advance the catheter through the nucleus pulposus and around the inner wall of the annulus fibrosus. Absolute penetration ability will vary with sharpness and stiffness of the tip of the catheter, but in all cases a catheter of the present invention will advance more readily through the nucleus pulposus than through the annulus fibrosus.

In preferred embodiments, the intradiscal section of the catheter further has differential bending ability in two orthogonal directions at right angles to the longitudinal axis. This causes the catheter to bend along a desired plane (instead of at random). Also when a torsional (twisting) force is applied to the proximal end of the catheter to re-orient the distal end of the catheter, controlled advancement of the catheter in the desired plane is possible.

A further component of the catheter is a functional element located in the intradiscal section for diagnosis or for adding energy and adding and/or removing material at the selected location of the disc where the annular tear is to be treated, or some other therapeutic action is to be carried out. The apparatus allows the functional element to be controllably guided by manipulation of the proximal end of the catheter into a selected location for localized diagnosis and/or treatment of a portion of the disc, such as, for example, the annular fissure.

The method of the invention which involves manipulating disc tissue at the annular fissure or other selected location, is easily carried out with an apparatus of the invention. An introducer is provided that is located in a patient's body so that its proximal end is external to the body and the distal opening of its lumen is internal to the body and (1) internal to the annulus fibrosus or (2) adjacent to an annular opening leading to the nucleus pulposus, such as an annular tear or trocar puncture that communicates with the nucleus pulposus. The catheter is then slid into position in and through the introducer lumen so that the functional element in the catheter is positioned at the selected location of the disc by advancing or retracting the catheter in the introducer lumen and optionally twisting the proximal end of the catheter to precisely navigate the catheter. By careful selection of the rigidity of the catheter and by making it sufficiently blunt to not penetrate the annulus fibrosus, and by careful selection of the flexibility in one plane versus the orthogonal plane, the distal portion of the catheter will curve along the inner wall of the annulus fibrosus as it is navigated and is selectively guided to an annular tear or other selected location(s) in the disc. Energy is applied and/or material is added or removed at the selected location of the disc via the functional element.

Each of the elements of the apparatus and method will now be described in more detail. However, a brief description of disc anatomy is provided first, as sizes and orientation of structural elements of the apparatus and operations of the method can be better understood in some cases by reference to disc anatomy.

The annulus fibrosus is comprised primarily of tough fibrous material, while the nucleus pulposus is comprised primarily of an amorphous colloidal gel. There is a transition zone between the annulus fibrosus and the nucleus pulposus made of both fibrous-like material and amorphous colloidal gel. The border between the annulus fibrosus and the nucleus pulposus becomes more difficult to distinguish as a patient ages, due to degenerative changes. This process may begin as early as 30 years of age. For purposes of this specification, the inner wall of the annulus fibrosus can include the young wall comprised primarily of fibrous material as well as the transition zone which includes both fibrous material and amorphous colloidal gels (hereafter collectively referred to as the "inner wall of the annulus fibrosus"). Functionally, that location at which there is an increase in resistance to catheter penetration and which is sufficient to cause bending of the distal portion of the catheter into a radius less than that of the internal wall of the annulus fibrosus is considered to be the "inner wall of the annulus fibrosus".

As with any medical instrument and method, not all patients can be treated, especially when their disease or injury is too severe. There is a medical gradation of degenerative disc disease (stages 1-5). See, for example, Adams et al., "The Stages of Disc Degeneration as Revealed by Discograms," J. Bone and Joint Surgery, 68, 36-41 (1986). As these grades are commonly understood, the methods of instrument navigation described herein would probably not be able to distinguish between the nucleus and the annulus in degenerative disease of grade 5. In any case, most treatment is expected to be performed in discs in stages 3 and 4, as stages 1 and 2 are asymptomatic in most patients, and stage 5 may require disc removal and fusion.

Figure 2:
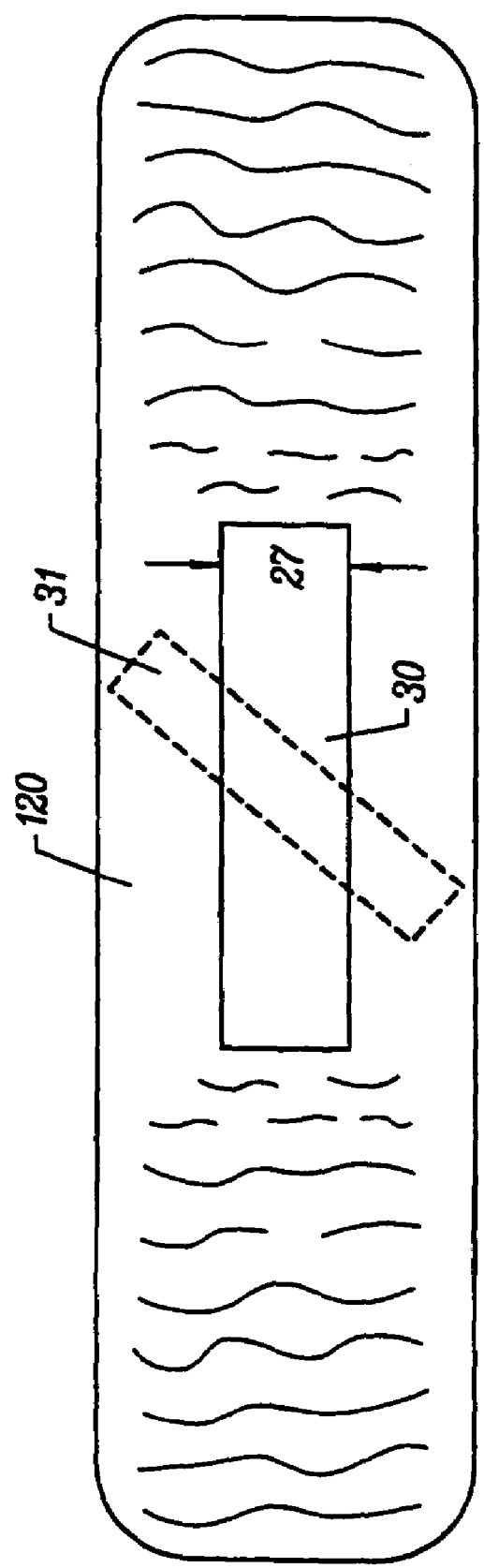
FIG. 2 is a second cross-sectional view of an intervertebral disc illustrating a disc plane of the intervertebral disc and an inferior/superior plane.

Some of the following discussion refers to motion of the catheter inside the disc by use of the terms "disc plane" "oblique plane" and "cephalo-caudal plane." These specific terms refer to orientations of the catheter within the intervertebral disc. Referring now to FIG. 2 (which shows a vertical cross-section of a disc), a disc plane 30 of the intervertebral disc is generally a plane of some thickness 27 within the nucleus pulposus 120 orthogonal to the axis formed by the spinal column (i.e., such a disc plane is substantially horizontal in a standing human, corresponding to the "flat" surface of a vertebra). A oblique plane 31 extends along any tilted orientation relative to axial plane 30; however, when the plane is tilted 90°, such a plane would be substantially vertical in a standing human and is referred to as a cephalo-caudal plane. Reference is made to such planes to describe catheter movements with respect to the disc plane. In various embodiments, disc plane 30 has a thickness no greater than the thickness of the intervertebral disc, preferably a thickness no greater than 75% of a thickness of the intervertebral disc, and more preferably a thickness no greater than 50% of a thickness of the intervertebral disc. Movement of the intradiscal portion 16 of catheter 14 is confined within a disc plane by the physical and mechanical properties of the intradiscal portion 16 during advancement of the catheter when the bending plane of the catheter is aligned with the disc plane until some additional force is applied to the catheter by the physician. A twisting force (which can be applied mechanically, electrically, or by any other means) acting on the proximal end of the catheter changes the forces acting on the distal end of the catheter so that the plane of the catheter bend can be angled relative to the disc plane as the catheter is advanced. Thus, the physician can cause the distal end of the catheter to move up or down, depending on the direction of the twist.

Turning now to the introducer, a detailed description of an entire apparatus should not be necessary for those skilled in the art of percutaneous procedures and the design of instruments intended for such use. The method of the invention can also be carried out with endoscopic instruments, and an endoscopic apparatus having structural parts that meet the descriptions set forth in this specification would also be an apparatus of the invention.

In general, a device of the invention can be prepared in a number of different forms and can consist (for example) of a single instrument with multiple internal parts or a series of instruments that can be replaceably and sequentially inserted into a hollow fixed instrument (such as a needle) that guides the operational instruments to a selected location, such as, for example, an annular fissure, in or adjacent to an intervertebral disc. Because prior patents do not fully agree on how to describe parts of percutaneous instruments, terminology with the widest common usage will be used.

The introducer, in its simplest form, can consist of a hollow needle-like device (optionally fitted with an internal removable obturator or trocar to prevent clogging during initial insertion) or a combination of a simple exterior cannula that fits around a trocar. The result is essentially the same: placement of a hollow tube (the needle or exterior cannula after removal of the obturator or trocar, respectively) through skin and tissue to provide access into the annulus fibrosus. The hollow introducer acts as a guide for introducing instrumentation. More complex variations exist in percutaneous instruments designed for other parts of the body and can be applied to design of instruments intended for disc operations. Examples of such obturators are well known in the art. A particularly preferred introducer is a 17- or 18-gauge, thin-wall needle with a matched obturator, which after insertion is replaced with a catheter of the present invention.

Figure 3:
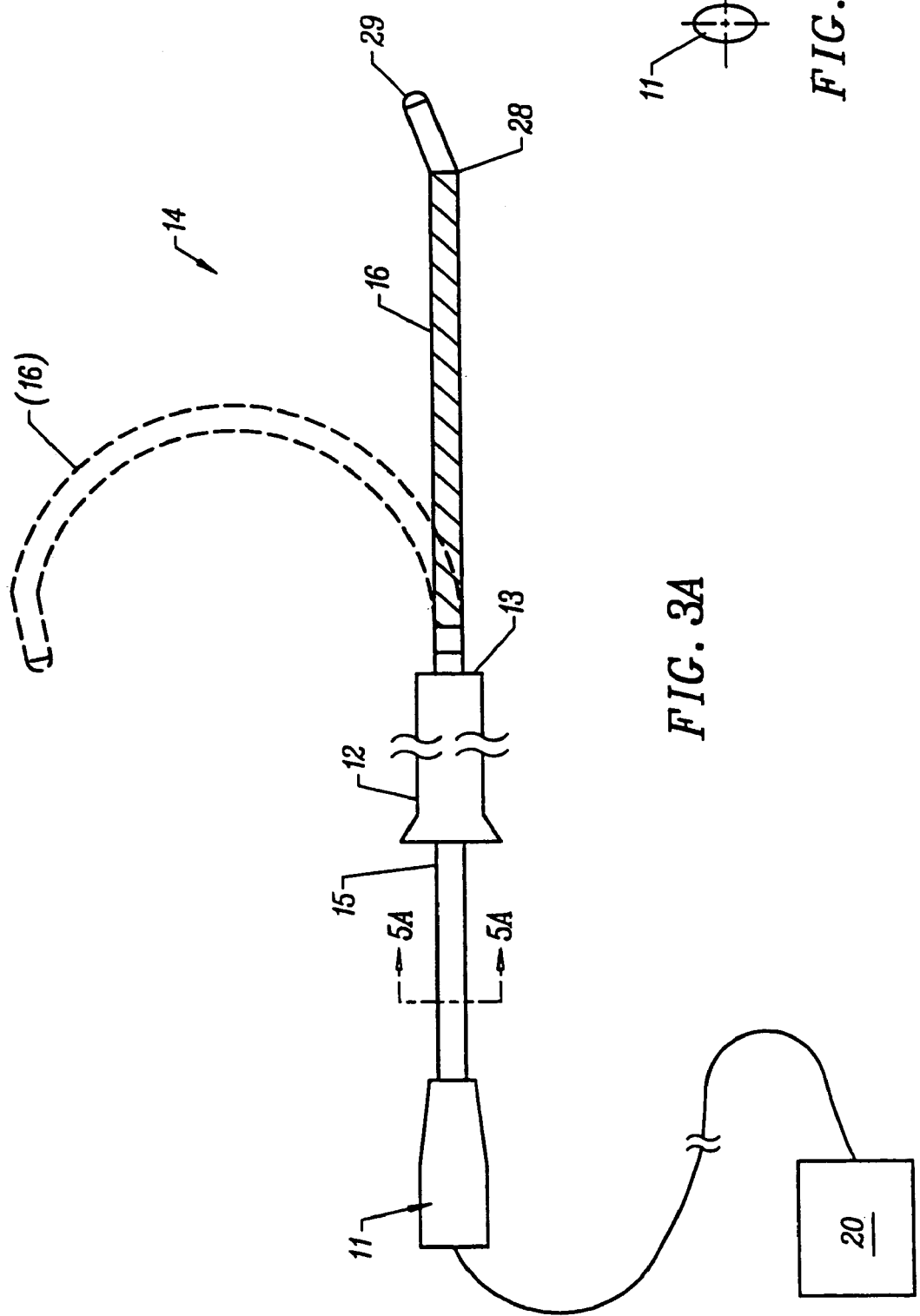
FIG. 3(a) is a plan view of an introducer and an instrument of the invention in which solid lines illustrate the position of the instrument in the absence of bending forces and dotted lines indicate the position the distal portion of the instruments would assume under bending forces applied to the intradiscal section of the instrument.
FIG. 3(b) is an end view of the handle of the embodiment shown in FIG. 3(a).

Referring now to the figures, FIGS. 3(a) and 3(b) illustrate one embodiment of a catheter 14 of the invention as it would appear inserted into an introducer 12. The apparatus shown is not to scale, as an exemplary apparatus (as will be clear from the device dimensions below) would be relatively longer and thinner; the proportions used in FIG. 3(a) were selected for easier viewing by the reader. The distal portion of an intervertebral apparatus operates inside an introducer 12 having an internal introducer lumen 13. A flexible, movable catheter 14 is at least partially positionable in the introducer lumen 13. Catheter 14 includes a distal end section 16 referred to as the intradiscal section, which is designed to be the portion of the catheter that will be pushed out of the introducer lumen and into the nucleus pulposus, where movement of the catheter will be controlled to bring operational portions of the catheter into the selected location (s) within the disc, such as, for example, the annular tear. In FIG. 3(a), dashed lines are used to illustrate bending of the intradiscal portion of the catheter as it might appear under use, as discussed in detail later in the specification. FIG. 3(b) shows an end view of handle 11 at the proximal end of the catheter, with the handle 11 having an oval shape to indicate the plane of bending, also discussed in detail later in the specification. Other sections and properties of catheter 14 are described later.

For one embodiment suitable for intervertebral discs, the outer diameter of catheter 14 is in the range of 0.2 to 5 mm, the total length of catheter 14 (including the portion inside the introducer) is in the range of 10 to 60 cm, and the length of introducer 12 is in the range of 5 to 50 cm. For one preferred embodiment, the catheter has a diameter of 1 mm, an overall length of 30 cm, and an introduced length of 15 cm (for the intradiscal section). With an instrument of this size, a physician can insert the catheter for a distance sufficient to reach selected location(s) in the nucleus of a human intervertebral disc.

Figure 4:
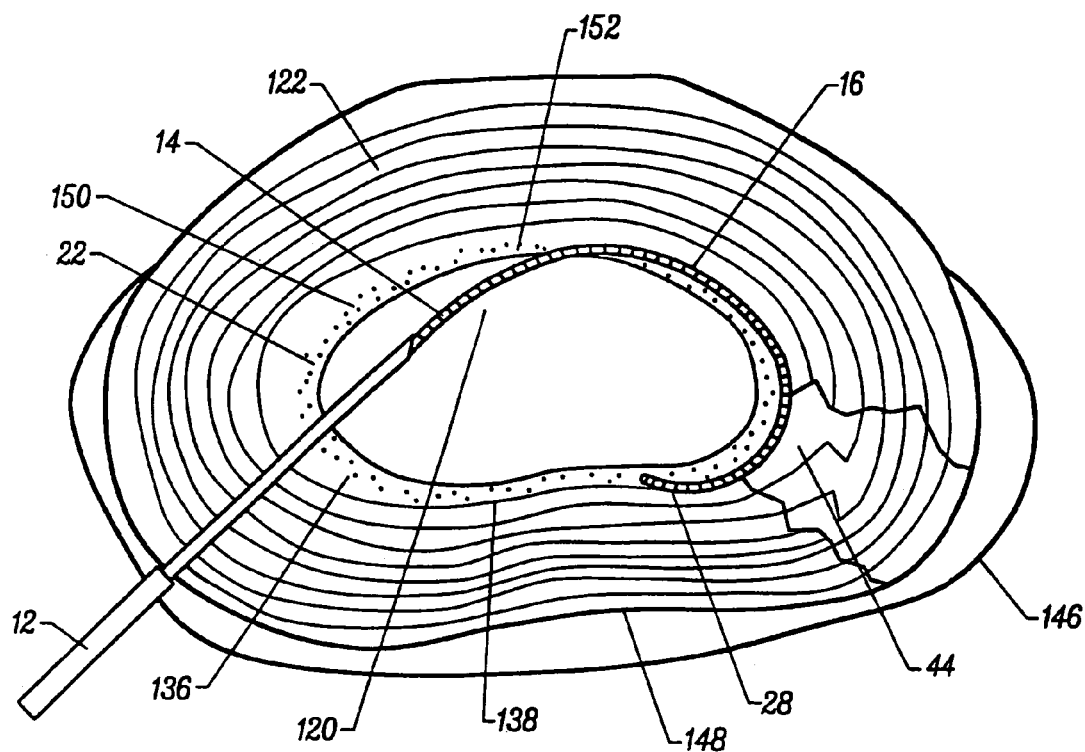
FIG. 4 is a cross-sectional view of an intervertebral disc with a portion of the intervertebral apparatus of the present invention inserted in the intervertebral disc.

FIG. 4 illustrates the anatomy of an intervertebral disc and shows an apparatus of the invention inserted into a disc. Structures of the disc are identified and described by these anatomical designations: the posterior lateral inner annulus 136, posterior medial inner annulus 138, annulus fibrosus 122/nucleus pulposus 120 interface, the annulus/dural interface 146, annulus/posterior longitudinal ligament interface 148, anterior lateral inner annulus 150, and the anterior medial inner annulus 152.

Referring again to FIG. 4, the mechanical characteristics of intradiscal section 16 of catheter 14 are selected to have (1) sufficient column strength along the longitudinal axis of the catheter to avoid collapse of the catheter and (2) different flexural strengths along the two axes orthogonal to the longitudinal axis to allow controlled bending of the catheter. These parameters make the catheter conformable and guidable along inner wall 22 of an annulus fibrosus 122 to reach selected location(s), such as the posterior medial annulus 138.

Specific mechanical characteristics of particular designs will be described later in the examples that follow. Generally, however, the necessary design features can be selected (in an interrelated fashion) by first providing the intradiscal section of the catheter with sufficient column strength to be advanceable through normal human nucleus pulposus and around the inner wall of the annulus fibrosus without collapse. Here "collapse" refers to bending sufficient to inhibit further advancement at the tip. Advancement of the tip is restricted by 1) sliding through the normal gelatinous nucleus pulposus, 2) contacting denser clumps of nucleus pulposus and 3) curving and advancing along the inner wall of the annulus. Column strength can be increased in many ways known in the art, including but not limited to selecting materials (e.g., metal alloy or plastic) with a high resistance to bending from which to form the catheter, forming the structure of the catheter with elements that add stiffening (such as bracing), and increasing the thickness of the structural materials. Column strength can be decreased to favor bending by selecting the opposite characteristics (e.g., soft alloys, hinging, and thin structural elements).

When the catheter collapses, the physician feels an abrupt decrease in resistance. At that time, the catheter forms one or more loops or kinks between the tip of the introducer and the distal tip of the catheter.

Particularly preferred for locations, such as, for example, annular tears, at the posterior of the annulus, the tip 28 of intradiscal section 16 is biased or otherwise manufactured so that it forms a pre-bent segment prior to contact with the annulus fibrosus as shown in FIG. 3(a). The bent tip will cause the intradiscal section to tend to continue to bend the catheter in the same direction as the catheter is advanced. This enhanced curving of a pre-bent catheter is preferred for a catheter that is designed to reach a posterior region of the nucleus pulposus; however, such a catheter must have sufficient column strength to prevent the catheter from collapsing back on itself.

The intradiscal section not only must allow bending around the relatively stronger annulus fibrosus in one direction, but also resist bending in the orthogonal direction to the plane in which bending is designed to occur. By twisting the proximal end of a catheter and thus controlling the orientation of the plane of bending while concurrently controlling the advancement of the catheter through the nucleus, a physician can navigate the catheter and its instrumentation within the disc.

The bending stiffness of the intradiscal section as measured in Taber stiffness units (using a length of the inventive catheter as the test strip rather than the standard dimension, homogeneous-material test strip) should be in the range of 2-400 units (in a 0-10,000 unit range) in the desired bending plane, preferably 3-150 units. In preferred embodiments, stiffness is in the range of 4-30 units in the desired bending plane. In all cases, the bending stiffness preferably is 2-20 times higher for bending in the orthogonal direction.

The column or compressive strength of the intradiscal section (force required to buckle a segment whose length is 25 or more times its diameter) is in the range of 0.05 to 4 kg, preferably 0.05 to 2 kg. In the most preferred embodiments, it is in the range of 0.1 to 1 kg. In the proximal shaft section (i.e., the part of the catheter proximal to the intradiscal section), this strength is in the range of 0.1 to 25 kg, preferably 0.2 to 7 kg. In the most preferred embodiments, it is in the range of 0.7 to 4 kg.

Returning now to FIG. 4, intradiscal section 16 is guidable and can reach the posterior, the posterior lateral, and the posterior medial regions of the posterior wall of the annulus fibrosus, as well as other selected section(s) on or adjacent to inner wall 22. In order to move the functional section of the catheter into a desired nucleus location, intradiscal section 16 is first positioned in the nucleus pulposus 120 by means of the introducer.

In most uses, introducer 12 pierces annulus fibrosus 122 and is advanced through the wall of the annulus fibrosus into the nucleus pulposus. In such embodiments, introducer 12 is then extended a desired distance into nucleus pulposus 120. Catheter 14 is advanced through a distal end of introducer 12 into nucleus pulposus 120. Advancement of the catheter 14, combined with increased resistance to advancement at the annulus fibrosus, causes the tip of the intradiscal section to bend relative to the longitudinal axis of introducer 12 when the intradiscal section contacts the inner wall of the annulus fibrosus 122. Catheter 14 is navigated along inner wall 22 of annulus fibrosus 122 to selected site(s) of inner wall 22 or within nucleus pulposus 120. For example, intradiscal section 16 can be positioned in or adjacent to a fissure or tear 44 of annulus fibrosus 122.

The distal portion 28 of intradiscal section 16 is designed to be incapable of piercing the annulus fibrosus 122. The inability of distal portion 28 to pierce the annulus can be the result of either shape of the tip 29 or flexibility of distal portion 28, or both. The tip 29 is considered sufficiently blunt when it does not penetrate the annulus fibrosus but is deflected back into the nucleus pulposus or to the side around the inner wall of the annulus when the tip 29 is advanced. The tip can be made with a freely rotating ball. This embodiment provides not only a blunt surface but also a rolling contact to facilitate navigation.

Many percutaneous and endoscopic instruments designed for other purposes can be adapted for use in this invention. This permits other functions at the desired location after the catheter is advanced to that position. For example, cutting edges and sharp points can be present in the distal portion 28 if they can be temporarily masked by a covering element. However, such devices must be sufficiently flexible and thin to meet the design characteristics described in this specification.

In another embodiment an introducer 12 pierces the skin and reaches an exterior of annulus fibrosus 122. A rigid and sharp trocar is then advanced through introducer 12, to pierce annulus fibrosus 122 and enter the disc. The trocar is then removed and catheter 14 is advanced through a distal end of introducer 12, following the path created by the trocar in annulus fibrosus 122 beyond the end of the introducer. In such cases, the introducer is outside the annulus fibrosus 122 and only the catheter with its guidable distal portion 16 is present inside the disc. The physician can manipulate the proximal portion 15 of the catheter to move the distal portion of the catheter to a selected location for diagnosing or treating the nucleus pulposus 120 or the inner wall 22 of the annulus fibrosus 122, such as, for example, a fissure of the annulus fibrosus 122.

Catheter 14 is not always pre-bent as shown in FIG. 3(a), but optionally can include a biased distal portion 28 if desired. "Pre-bent" or "biased" means that a portion of the catheter (or other structural element under discussion) is made of a spring-like material that is bent in the absence of external stress but which under selected stress conditions (for example, while the catheter is inside the introducer), is linear. Such a biased distal portion can be manufactured from either spring metal or superelastic memory material (such as Tinel® nickel-titanium alloy, Raychem Corp., Menlo Park Calif.). The introducer (at least in the case of a spring-like material for forming the catheter) is sufficiently strong to resist the bending action of the bent tip and maintain the biased distal portion in alignment as it passes through the introducer. Compared to unbiased catheters, a catheter with a biased distal portion 28 encourages advancement of intradiscal section 16 substantially in the direction of the bend relative to other lateral directions as shown by the bent location of intradiscal section 16 indicated by dashed lines in FIG. 3(a). That is, biased distal portion 28 permits advancement of intradiscal section 16 substantially in only one lateral direction relative to the longitudinal axis of introducer 12. More generally, embodiments of the intradiscal section may resist bending in at least one direction. Biasing the catheter tip also further decreases likelihood that the tip 29 will be forced through the annulus fibrosus under the pressure used to advance the catheter.

In one embodiment, the outer diameter of catheter 14 is in the range of 0.01 to 0.200 inches, the total length of catheter 14 is in the rage of 5 to 24 inches, and the length of introducer 12 is 2 to 20 inches. The total length of catheter 14 (including the portion inside the introducer) may be in the range of 5 to 24 inches, and the length of introducer 12 may be 2 to 20 inches. The intradiscal section may have a length at least one-half of the diameter of the nucleus pulposus. One embodiment of the introducer is an 18- or 17-gauge, thin-wall needle with a matched stylet.

In addition to biasing a catheter tip prior to insertion into an introducer, a catheter tip can be provided that is deflected by mechanical means, such as a wire attached to one side of the tip that deflects the tip in the desired direction upon application of force to the proximal end of the deflection wire. Any device in which bending of the tip of a catheter of the invention is controlled by the physician is "actively steerable." In addition to a tip that is actively steerable by action of a wire, other methods of providing a bending force at the tip can be used, such as hydraulic pressure and electromagnetic force (such as heating a shaped memory alloy to cause it to contract). Any of a number of techniques can be used to provide selective bending of the catheter in one lateral direction.

Figure 5A:
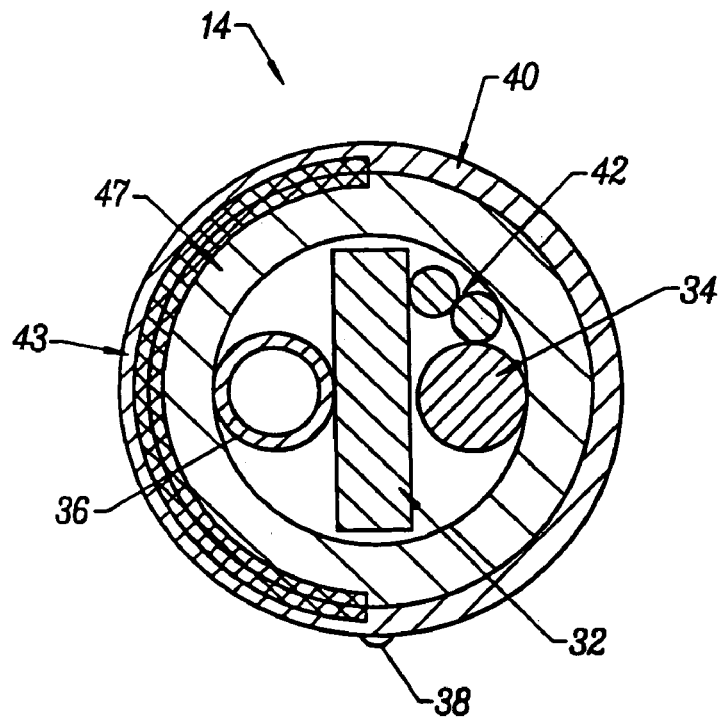
FIG. 5(a) is a cross-sectional view of the intervertebral segment of the embodiment of the invention shown in FIG. 3(a) taken along the line 5(a)-5(a) of FIG. 3(a).

Referring now to FIG. 5(a), a guiding mandrel 32 can be included both to add rigidity to the catheter and to inhibit movement of catheter 14 in the inferior and superior directions while positioned and aligned in the disc plane of a nucleus pulposus 120. This aids the functions of preventing undesired contact with a vertebra and facilitating navigation. The mandrel can be flattened to encourage bending in a plane (the "plane of the bend") orthogonal to the "flat" side of the mandrel. "Flat" here is a relative term, as the mandrel can have a D-shaped cross-section, or even an oval or other cross-sectional shape without a planar face on any part of the structure. Regardless of the exact configuration, bending will preferentially occur in the plane formed by the principal longitudinal axis of the mandrel and a line connecting the opposite sides of the shortest cross-sectional dimension of the mandrel (the "thin" dimension). To provide sufficient resistance to the catheter bending out of the desired plane while encouraging bending in the desired plane, the minimum ratio is 1.25:1 ("thickest" to "thinnest" cross-sectional dimensions along at least a portion of the intradiscal section). The maximum ratio is 20:1, with the preferred ratio being between 1.5:1 and 16:3, more preferably between 2:1 and 3.5:1. These ratios are for a solid mandrel and apply to any material, as deflection under stress for uniform solids is inversely proportional to the thickness of the solid in the direction (dimension) in which bending is taking place. For other types of mandrels (e.g., hollow or non-uniform materials), selection of dimensions and/or materials that provide the same relative bending motions under stress are preferred.

A catheter of the present invention is designed with sufficient torsional strength (resistance to twisting) to prevent undesired directional movement of the catheter. Mandrels formed from materials having tensile strengths in the range set forth in the examples of this specification provide a portion of the desired torsional strength. Other materials can be substituted so long as they provide the operational functions described in the examples and desired operating parameters.

While the mandrel can provide a significant portion of the column strength, selective flexibility, and torsional strength of a catheter, other structural elements of the catheter also contribute to these characteristics. Accordingly, it must be kept in mind that it is the characteristics of the overall catheter that determine suitability of a particular catheter for use in the methods of the invention. For example, a mandrel that does not have sufficient torsional strength when acting alone can be combined with another element, such as anti-twisting outer sheath 40 or inserting/advancing a second mandrel, to provide a catheter of the invention. Similarly, components inside the catheter, such as a heating element or potting compound, can be used to strengthen the catheter or provide directional flexibility at the locations of these elements along the catheter.

It is not necessary that the guiding mandrel 32 be flattened along its entire length. Different mandrels can be designed for different sized discs, both because of variations in disc sizes from individual to individual and because of variations in size from disc to disc in one patient. The bendable portion of the mandrel is preferably sufficient to allow intradiscal portion 16 of the catheter to navigate at least partially around the circumference of the inner wall of the annulus fibrosus (so that the operational functions of the catheter can be carried out at desired location(s) along the inner wall of the annulus fibrosus). Shorter bendable sections are acceptable for specialized instruments. In most cases, a flattened distal portion of the mandrel of at least 10 mm, preferably 25 mm, is satisfactory. The flattened portion can extend as much as the entire length of the mandrel, with some embodiments being flattened for less than 15 cm, in other cases for less than 10 cm, of the distal end of the guide mandrel.

The intradiscal section of the catheter can be guided to conform sufficiently to the inner wall of the annulus fibrosus to contact multiple locations of the inner wall. The intradiscal section and/or distal portion are positionable to any selected site around and/or adjacent to the inner wall of the annulus fibrosus for the delivery of RF energy. The intradiscal section and/or distal portion can deliver electromagnetic energy to, e.g., heat tissue and thereby reduce pain at a selected site (for example, any portion of the annulus fibrosus).

In preferred embodiments the guide mandrel or other differential bending control element is maintained in a readily determinable orientation by a control element located at the proximal end of the catheter. The orientation of the direction of bending and its amount can be readily observed and controlled by the physician. One possible control element is simply a portion of the mandrel that extends out of the proximal end of the introducer and can be grasped by the physician, with a shape being provided that enables the physician to determine the orientation of the distal portion by orientation of the portion in the hand. For example, a flattened shape can be provided that mimics the shape at the distal end (optionally made larger to allow better control in the gloved hand of the physician, as in the handle 11 of FIG. 3(b)). More complex proximal control elements capable of grasping the proximal end of the mandrel or other bending control element can be used if desired, including but not limited to electronic mechanical, and hydraulic controls for actuation by the physician.

The guide mandrel can also provide the function of differential flexibility by varying the thickness in one or more dimensions (for example, the "thin" dimension, the "thick" dimension, or both) along the length of the mandrel. A guide mandrel that tapers (becomes gradually thinner) toward the distal tip of the mandrel will be more flexible and easier to bend at the tip than it is at other locations along the mandrel. A guide mandrel that has a thicker or more rounded tip than more proximal portions of the mandrel will resist bending at the tip but aid bending at more proximal locations. Thickening (or thinning) can also occur in other locations along the mandrel. Control of the direction of bending can be accomplished by making the mandrel more round, i.e., closer to having 1:1 diameter ratios; flatter in different sections of the mandrel; or by varying the absolute dimensions (increasing or decreasing the diameter). Such control over flexibility allows instruments to be designed that minimize bending in some desired locations (such as the location of connector of an electrical element to avoid disruption of the connection) while encouraging bending in other locations (e.g., between sensitive functional elements). In this manner, a catheter that is uniformly flexible along its entire length, is variably flexibility along its entire length, or has alternating more flexible and less flexible segment(s), is readily obtained simply by manufacturing the guide mandrel with appropriate thickness at different distances and in different orientations along the length of the mandrel. Such a catheter will have two or more different radii of curvature in different segments of the catheter under the same bending force.

In some preferred embodiments, the most distal 3 to 40 mm of a guide mandrel is thinner relative to central portions of the intradiscal section to provide greater flexibility, with the proximal 10 to 40 mm of the intradiscal section being thicker and less flexible to add column strength and facilitate navigation.

The actual dimensions of the guide mandrel will vary with the stiffness and tensile strength of the material used to form the mandrel. In most cases the mandrel will be formed from a metal (elemental or an alloy) or plastic that will be selected so that the resulting catheter will have characteristics of stiffness and bending that fall within the stated limits. Additional examples of ways to vary the stiffness and tensile strength include transverse breaks in a material, advance of the material so that it "doubles up," additional layers of the same or different material, tensioning or relaxing tension on the catheter, and applying electricity to a memory metal.

Figure 5B:
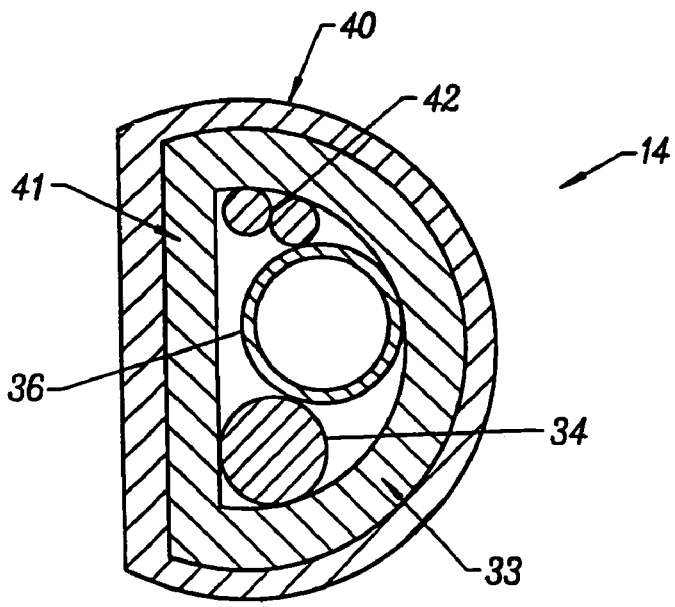
FIG. 5(b) is a cross-sectional view of the intervertebral segment of a second embodiment of the present invention having a combined wall/guiding mandrel.

As illustrated in FIG. 5(b), in some embodiments of an apparatus of the invention, guiding mandrel is combined with at least a portion of the catheter 14 to form a structure which provides the functions of both, a wall/mandrel 41. In this figure, the wall/mandrel 41 of catheter 14 can be varied in dimensions as described in the previous section of this specification directed to a separate mandrel, with the same resulting changes in function. For example, changing the thickness of the wall/mandrel 41 that functions as the mandrel portion change, the flexibility and preferred direction of bending of the catheter. In many cases, the wall/mandrel 41 will be thinner than other portions of the catheter wall 33 so that wall/mandrel 41 controls bending. Alternatively, wall/mandrel 41 can be formed of a different material than the other portions 33 of the catheter walls (i.e., one with a lower tensile and/or flexural strength) in order to facilitate bending.

Returning now to FIG. 5(a), the guiding mandrel 32 is generally located in the interior of catheter 14, where it shares space with other functional elements of the catheter. For example and as shown in FIG. 5(a), thermal energy delivery device lumen 34 can receive any of a variety of different couplings from an energy source 20 to a thermal energy delivery device (functional element) further along the catheter, including but not limited to a wire or other connector between thermal energy elements. Alternatively or concurrently, hollow lumen(s) 36 for delivery and/or removal of a fluid or solid connectors for application of a force to a mechanical element can be present, so no limitation should be placed on the types of energy, force, or material transporting elements present in the catheter. These are merely some of the possible alternative functional elements that can be included in the intradiscal portion of the catheter. Accordingly, a general description will now be given of some of the possible functional elements.

To facilitate a catheter in performing some function on disc or nearby tissue, such as, for example, applying electromagnetic energy to controllably heat disc tissue at selected location(s) inside the disc, or repairing tears or fissures in a disc by operation of the instrument at the tear location adjacent to or inside the disc, a functional element is provided in or on the catheter. One such element is a functional electromagnetic probe such as an RF electrode.

Non-limiting examples of functional elements include any element capable of aiding diagnosis, delivering energy, or delivering or removing a material from a location adjacent the element's location in the catheter, such as an opening in the catheter for delivery of a fluid (e.g., dissolved collagen to seal the fissure) or for suction, a thermal energy delivery device (heat source), a mechanical grasping tool for removing or depositing a solid, a cutting tool (which includes all similar operations, such as puncturing), a sensor for measurement of a function (such as electrical resistance, temperature, or mechanical strength), or a functional element having a combination of these functions.

The functional element can be at varied locations in the intradiscal portion of the catheter, depending on its intended use. Multiple functional elements can be present such as multiple functional elements of different types (e.g., a heat source and a temperature sensor) or multiple functional elements of the same type (e.g., multiple heat sources, such as RF elements, spaced along the intradiscal portion).

One of the functional elements present on intradiscal section 16 can be an RF electrode. A variety of different types and shapes of RF electrodes can be used. The intradiscal section electrode can be monopolar or bipolar. In one embodiment, the RF electrode is positioned proximal to the distal portion of intradiscal section 16 so that there is no substantial delivery of energy at the distal portion, which can then perform other functions without being constrained by being required to deliver RF energy. The RF electrode is coupled to RF generating source 20 through the catheter. The RF electrode is positioned on an external surface of intradiscal section 16. A variety of different types of electromagnetic energy can be delivered to tissue wherein heating is caused. These include not only RF but also coherent and incoherent light, microwave, and ultrasound.

One of the possible functional elements present on intradiscal section 16 is a thermal energy delivery device 18. A variety of different types of thermal energy can be delivered including but not limited to resistive heat, radiofrequency (RF), coherent and incoherent light, microwave, ultrasound and liquid thermal jet energies. In one embodiment, thermal energy delivery device 18 is positioned proximal to the distal portion of intradiscal section 16 so that there is no substantial delivery of energy at the distal portion, which can then perform other functions without being constrained by being required to provide energy (or resist the resulting heat).

Some embodiments have an interior infusion lumen 36. Infusion lumen 36 is configured to transport a variety of different media including but not limited to electrolytic solutions (such as normal saline), contrast media (such as Conray meglumine iothalamate), pharmaceutical agents, disinfectants, filling or binding materials such as collagens or cements, chemonucleolytic agents and the like, from a reservoir exterior to the patient to a desired location within the interior of a disc (i.e., the fissure). Further, infusion lumen 36 can be used as an aspiration lumen to remove nucleus material or excess liquid or gas (naturally present, present as the result of a liquefying operation, or present because of prior introduction) from the interior of a disc. When used to transport a fluid for irrigation of the location within the disc where some action is taking place (such as ablation, which generates waste materials), the infusion lumen is sometimes referred to as an irrigation lumen. Infusion lumen 36 can be coupled to medium reservoir 21 through the catheter (see FIG. 3(a)).

Included in the particular embodiment shown in FIG. 5(a) is one or more sensor lumens 42. An example is a wire connecting a thermal sensor at a distal portion of the catheter to control elements attached to a connector in the proximal handle 11 of the catheter.

Also included in the embodiment shown in FIG. 5(a) is an optional energy directing device 43 including but not limited to a thermal reflector, an optical reflector, thermal insulator, or electrical insulator. Energy directing device 43 is configured to limit thermal and/or electromagnetic energy delivery to a selected site of the disc and to leave other sections of the disc substantially unaffected. Energy directing device 43 can be positioned on an exterior surface of catheter intradiscal section 16 and/or catheter 14 as well as in an internal portion of the catheter intradiscal section 16 and/or catheter 14. For example, the energy can be directed to the walls of the fissure to cauterize granulation tissue and to shrink the collagen component of the annulus, while the nucleus is shielded from excess heat.

In one embodiment, catheter intradiscal section 16 and/or distal portion 28 are positionable to selected site(s) around and/or adjacent to inner wall 22 of annulus fibrosus 122 for the delivery of therapeutic and/or diagnostic agents including but not limited to, electromagnetic energy, electrolytic solutions, contrast media, pharmaceutical agents, disinfectants, collagens, cements, chemonucleolytic agents and thermal energy. Intradiscal section 16 is navigational and can reach the posterior, the posterior lateral, the posterior medial, anterior lateral, and anterior medial regions of the annulus fibrosus, as well as selected section(s) on or adjacent to inner wall 22.

In a preferred embodiment, intradiscal section 16 is positioned adjacent to the entire posterior wall of the disc. Sufficient thermal energy can then be delivered, for example, to selectively heat the posterior annulus to cauterize granulation tissue and shrink the collagen component of the wail around and adjacent to fissure 44 without undue damage to other portions of the intervertebral disc, particularly the nucleus. These actions help close the fissure in the annulus.

In the preferred embodiment of FIG. 5(a), markings 38 are visible on the portion of the catheter that is located during normal operation outside the body being acted upon, particularly for embodiments in which the proximal end of the catheter is designed to be directly manipulated by the hand of the physician. Advancement of the catheter into the introducer will advance the markings into the introducer thereby showing how far the catheter has been advanced into the nucleus. Such a visible marking 38 can be positioned on an exterior surface of the catheter or can be present on an interior surface and visible through a transparent outer covering or sheath. Preferred are visible markings every centimeter to aid the physician in estimating the catheter tip advancement.

If desired, visible markings can also be used to show twisting motions of the catheter to indicate the orientation of the bending plane of the distal portion of the catheter. It is preferred, however, to indicate the distal bending plane by the shape and feel of the proximal end of the catheter assembly. The catheter can be attached to or shaped into a handle 11 that fits the hand of the physician and also indicates the orientation of the distal bending plane. Both the markings and the handle shape thus act as control elements to provide control over the orientation of the bending plane; other control elements, such as plungers or buttons that act on mechanical, hydrostatic, electrical, or other types of controls, can be present in more complex embodiments of the invention.

Additionally, a radiographically opaque marking device can be included in the distal portion of the catheter (such as in the tip or at spaced locations throughout the intradiscal portion) so that advancement and positioning of the intradiscal section can be directly observed by radiographic imaging. Such radiographically opaque markings are preferred when the intradiscal section is not clearly visible by radiographic imaging, such as when the majority of the catheter is made of plastic instead of metal. A radiographically opaque marking can be any of the known (or newly discovered) materials or devices with significant opacity. Examples include but are not limited to a steel mandrel sufficiently thick to be visible on fluoroscopy, a tantalum/polyurethane tip, a gold-plated tip, bands of platinum, stainless steel or gold, soldered spots of gold and polymeric materials with radiographically opaque filler such as barium sulfate. A resistive heating element or an RF electrode(s) may provide sufficient radio-opacity in some embodiments to serve as a marking device.

A sheath 40 can optionally be positioned around catheter 14. Sheath 40 provides a flexible surface that is smooth and provides for easy introduction into a selected area within the disc. Sheath 40 can be made of a variety of different materials including but not limited to polyester, rayon, polyimide, polyurethane, polyethylene, polyamide and silicone. When visible markings are present to indicate the advancement of the catheter, either the sheath carries the markings, or the sheath is clear to reveal markings underneath.

The thermal energy delivery device can be a known RF electrode, such as a band or coil. Heating element 46 can be an RF electrode 46 positioned on and exterior of catheter 14. RF electrode 46 can be powered by an RF generator. The thermal energy delivery device can be made of a material that acts as an electrode. Suitable materials include but are not limited to stainless steel or platinum. The RF electrode is located on intradiscal section of catheter 14. Increasing levels of current conducted into the disc heats that tissue to greater temperature levels. A circuit can be completed substantially entirely at intradiscal section 16 (bipolar devices) or by use of a second electrode attached to another portion of the body (monopolar devices). In either case, a controllable delivery of RF energy is achieved.

Using an RF electrode, sufficient energy can be delivered to the intervertebral disc to heat tissue positioned adjacent to catheter 14. The amount of tissue heating is a function of (i) the amount of current passing through electrode 46, (ii) the length, shape, and/or size of heating electrode 46, (iii) the resistive properties of the tissue, and (iv) the use of cooling fluid to control temperature. The RF power supply 20 associated with heating electrode 46 can be battery based. Catheter 14 can be sterilized and can be disposable. Design of RF electrodes is within the skill of the art, and no special selection of electrode type or shape is generally required, although a particular shape or size can be selected for a particular function.

There can be two monopolar electrodes on the distal end of the RF probe. One electrode can occupy a portion of the side of the distal end and the other can be the distal-most tip of the RF probe. The electrodes can be operated independently to provide different tissue temperatures. In one configuration, the side electrode has a smaller area than the end electrode. If the side electrode receives the same power as the end electrode, it will provide more concentrated current and thus will produce more thermal energy. The end electrode will provide gentler, less concentrated current and will produce less thermal energy, for example, to shrink collagen in the annulus without denaturing the collagen.

Figure 6:
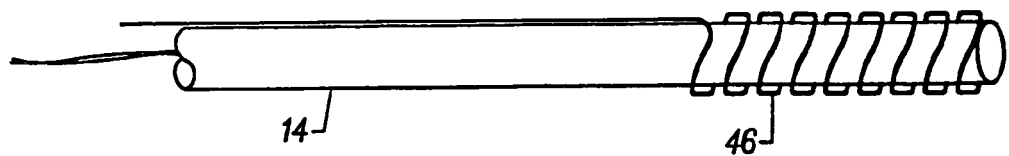
FIG. 6 is a perspective view of an embodiment of an apparatus of the present invention with a resistive heating coil positioned around an exterior of an intradiscal section of the catheter.

In one preferred embodiment, thermal energy delivery device 18 is a resistive heating device. As illustrated in FIG. 6, a heating coil 46 is positioned around an exterior of catheter 14. The heating element 46 need not be in the shape of a coil. For instance, the heating element can be in the form of a thin flexible circuit which is mountable on or in substantially one side of the intradiscal portion of the catheter. Heating element 46 is powered by a direct current source 20 (and less preferably a source of alternating current). Heating element is made of a material that acts as a resistor. Suitable materials include but are not limited to stainless steel, nickel/chrome alloys, platinum, and the like.

Figure 8:
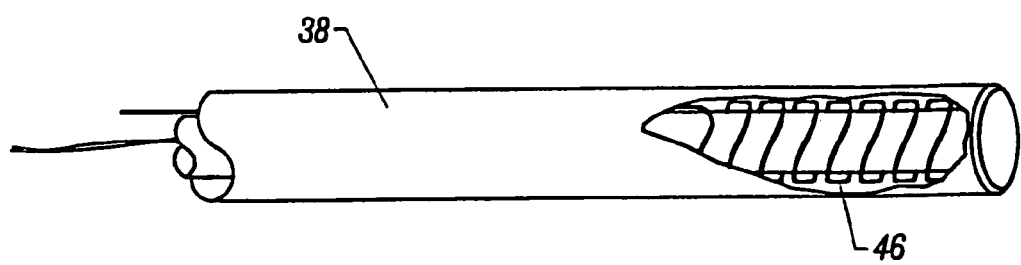
FIG. 8 is a partial cross-sectional view of an embodiment of the apparatus of the invention further including a sheath positioned around the resistive heating coil.

Preferably, the heating element is inside the intradiscal section of catheter 14 (FIG. 8). The resistive material is electrically insulated and substantially no current escapes into the body. With increasing levels of current, element 46 heats to greater temperature levels. Additionally, a circuit can be completed substantially entirely at intradiscal section 16 and a controllable delivery of thermal energy is achieved. In one embodiment, 2 watts pass through heating element 46 to produce a temperature of about 55° C. in a selected target such as fissure 44, 3 watts produces 65° C., 4 watts produces 75° C. and so on.

In another embodiment, thermal energy delivery device 18 is a radiofrequency electrode, such as a band or coil. As illustrated in FIG. 6, RF electrode 46 is positioned on an exterior of catheter 14. RF electrode 46 is powered by an RF generator. The electrode is made of suitable materials including but not limited to stainless steel or platinum. The RF electrode is located on intradiscal section of catheter 14. Increasing levels of current conducted into disc tissue heat that tissue to greater temperature levels. A circuit can be completed substantially entirely at intradiscal section 16 (bipolar device) or by use of a second electrode attached to another portion of the patient's body (monopolar device). In either case, a controllable delivery of RF energy is achieved.

In another embodiment sufficient energy is delivered to the intervertebral disc to heat and shrink the collagen component of the annulus but not ablate tissue adjacent to catheter 14.

With a resistive heating device, the amount of thermal energy delivered to the tissue is a function of (i) the amount of current passing through heating element 46, (ii) the length, shape, and/or size of heating element 46, (iii) the resistive properties of heating element 46, (iv) the gauge of heating element 46, and (v) the use of cooling fluid to control temperature. All of these factors can be varied individually or in combination to provide the desired level of heat. Power supply 20 associated with heating element 46 may he battery based. Catheter 14 can be sterilized and may be disposable.

Figure 7:
FIG. 7 is a partial cross-sectional view of an embodiment an apparatus of the invention illustrating a sensor positioned in an interior of the intradiscal section of the catheter.

Referring now to FIG. 7, a thermal sensor 48 may be positioned in an interior location of catheter 14. In another embodiment, thermal sensor 48 is positioned on an exterior surface of catheter 14. A thermal sensor can be used to control the delivery of energy to thermal energy delivery device 18. A potting material can be used to fix the position of thermal sensor 48 and provide a larger area from which to average the measured temperature. Thermal sensor 48 is of conventional design, including but not limited to a thermistor; T type thermocouple with a copper constant an junction; J type, E type, and K type thermocouples; fiber optics; resistive wires; IR detectors; and the like. Optionally, there may be a lumen 42 for the thermal sensor connection.

Figure 9:
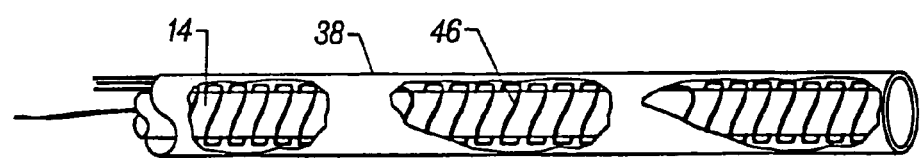
FIG. 9 is a partial cross-sectional view of an embodiment of the apparatus of FIG. 6 with multiple resistive heating coils.

As illustrated in FIG. 8, sheath 40 may be used to cover resistive heating element 46. A plurality of resistive heating elements 46 can be used (FIG. 9) in a catheter of the invention.

Figure 10:
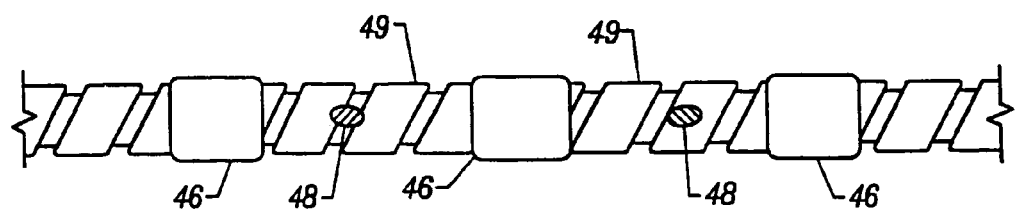
FIG. 10 is a plan view of an embodiment of the intradiscal section of a catheter of the invention with a helical structure.

Referring now to the embodiment shown in FIG. 10, thermal energy delivery device 18 comprises one or more resistive heating elements 46 coupled to a resistive heating energy source. Resistive heating elements 46 are positioned along intradiscal section 16 at locations where they controllably deliver thermal energy to selected structures, including granulation tissue in a fissure 44 and the annulus surrounding the fissure. Resistive heating elements 46 can be segmented and multiplexed so that only certain resistive heating elements, or combinations of resistive heating elements are activated at any one particular time. Thermal sensor 48 can be positioned between resistive heating elements 46 and/or at an exterior or interior location of catheter 14. In the embodiment illustrated in FIG. 10, catheter 14 can be prepared with a wound helical structure element 49 to increase flexibility and minimize kinking. However, other structures and geometries are suitable for catheter 14, including but not limited to a substantially smooth surface (and specifically including the device using an internal guide mandrel as previously described). For example, a sheath can be provided over the heating element, and the guiding mandrel inside the coil can be encapsulated in silicone potting material. The tubing flexibility and the silicone potting material prevent kinking. Additionally, sheath 40 can be positioned around catheter 14 and also around resistive heating elements 46 to afford a substantially smooth surface. Resistive heating element 46 can be at least partially covered by a thermally insulating material, for example, along one side of the catheter, to selectively heat disc tissue on the opposite side.

Figure 11:
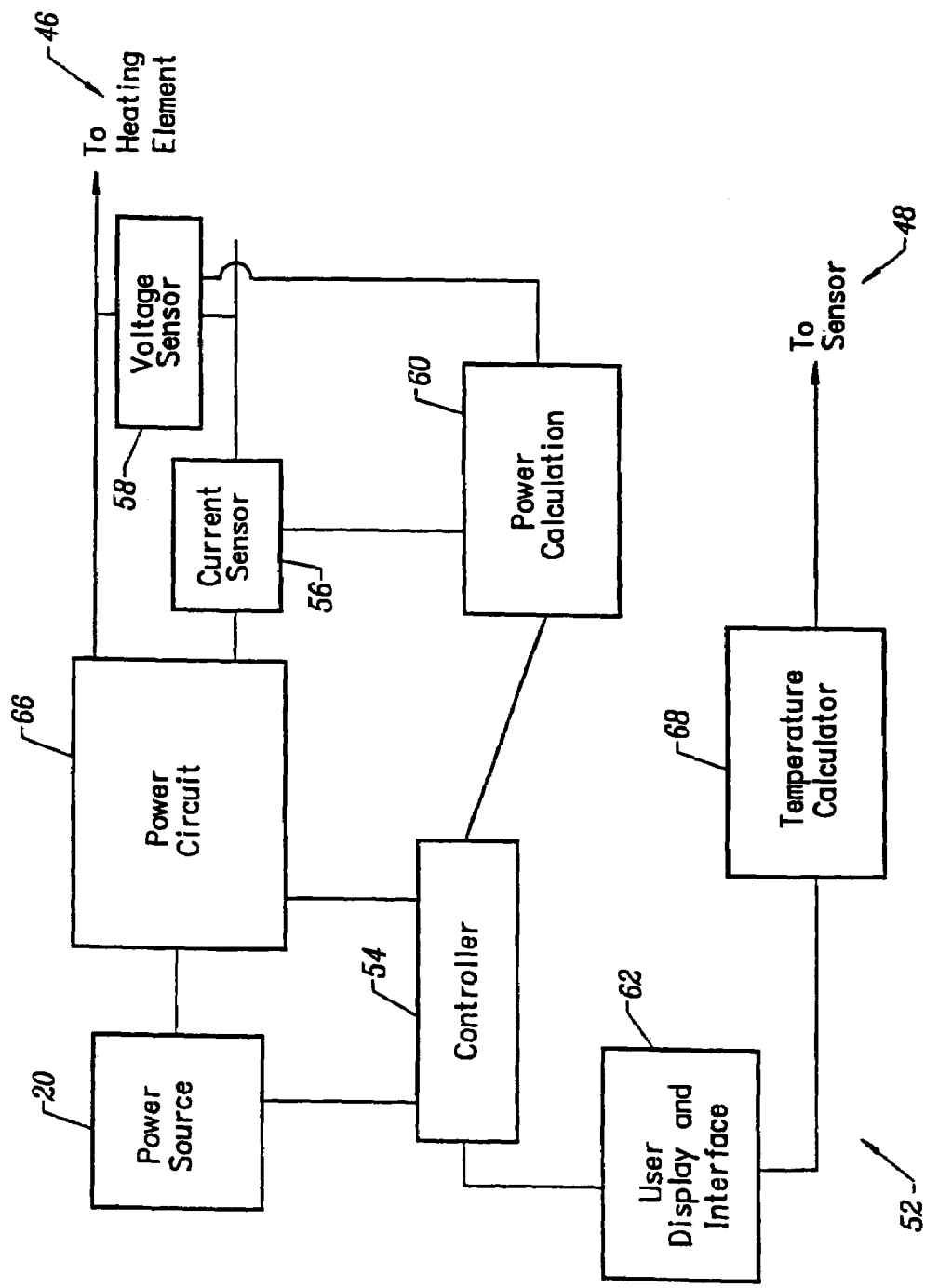
FIG. 11 is a block diagram of an open or closed loop feedback system that couples one or more sensors to an energy source.
Figure 12:
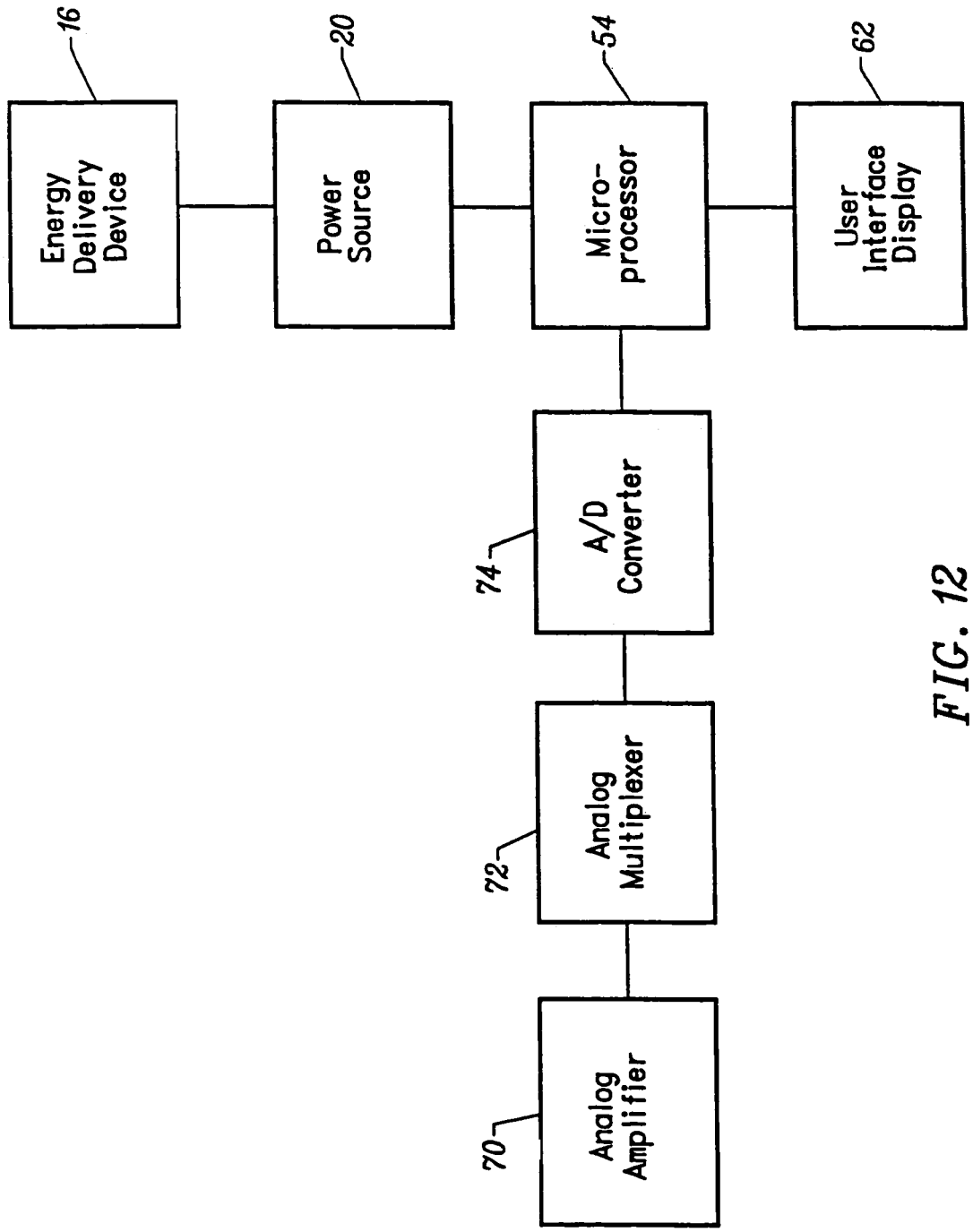
FIG. 12 is a block diagram of an embodiment illustrating an analog amplifier, analog multiplexer and microprocessor used with the feedback control system of FIG. 11.

Referring now to FIGS. 11 and 12, an open or closed loop feedback system 52 couples sensors 48 to energy source 20. As illustrated in FIG. 10, thermal energy delivery device 18 is a resistive heating element 46. It will be appreciated that the embodiments illustrated in FIGS. 10 and 11 are readily adaptable to other thermal energy delivery sources (e.g., for radiofrequency energy, the resistive heating element is replaced with insulated RF probe(s) and the energy source is an RF generator).

The temperature of the tissue or of element 46 (FIG. 10) is monitored by sensors 48, and the output power of energy source 20 adjusted accordingly. The physician can, if desired, override control system 52. A microprocessor can be included and incorporated in the closed or open loop system to switch power on and off, as well as to modulate the power. The closed loop system utilizes a microprocessor to serve as a controller 54 which acts to monitor the temperature and adjust the power accordingly. Alternatives to the microprocessor are, for example, analog control circuitry and a logic controller.

With the use of sensors 48 and feedback control system 52, a tissue adjacent to resistive heating elements 46 can be maintained at a desired temperature for a selected period of time without aberrant high temperature fluctuations. Each resistive heating element 46 can be connected to separate control and power supply resources, which generate an independent output for each resistive heating element 46. For example, a desired thermal output can be achieved by maintaining a selected energy at resistive heating elements 46 for a selected length of time.

When a resistive heating element 46 is used, current delivered through resistive heating element 46 can be measured by current sensor 56. Voltage can be measured by voltage sensor 58. Resistance and power are then calculated at power calculation device 60. These values can then be displayed at user interface and display 62. Signals representative of power and resistance values are received by a controller 54.

A control signal is generated by controller 54 that is related to the current and voltages. The control signal is used by power circuits 66 to adjust the power output in an appropriate amount in order to maintain the desired power delivered at respective resistive heating elements 46.

In a similar manner, temperatures detected at sensors 48 provide feedback for maintaining a selected power. The actual temperatures are measured at temperature measurement device 68, and the temperatures are displayed at user interface and display 62. A control signal is generated by controller 54 that is related to the actually measured temperature and a desired temperature. The control signal is used by power circuits 66 to adjust the power output in an appropriate amount in order to maintain the desired temperature delivered at the respective sensor 48. A multiplexer can be included to measure current, voltage, and temperature at the sensors 48, 56 and 58, so that appropriate energy can be delivered to resistive heating elements 46.

Controller 54 can be a digital or analog controller or a computer with software. When controller 54 is a computer, it can include a CPU coupled through a system bus. Included in this system can be a keyboard, a disc drive or other non-volatile memory system, a display, and other peripherals, as are known in the art. Also coupled to the bus can be a program memory and a data memory.

User interface and display 62 includes operator controls and a display. Controller 54 can be coupled to imaging systems well known in the art.

The output of current sensor 56 and voltage sensor 58 is used by controller 54 to maintain a selected power level at resistive heating elements 46. A predetermined profile of power delivered can be incorporated in controller 54, and a preset amount of energy to be delivered can also be profiled.

Circuitry, software, and feedback to controller 54 result in process control and in the maintenance of the selected power that is independent of changes in voltage or current. Control can include (i) the selected power and (ii) the duty cycle (wattage and on-off times). These process variables are controlled and varied while maintaining the desired delivery of power independent of changes in voltage or current, based on temperatures monitored at sensors 48.

In the embodiment shown, current sensor 56 and voltage sensor 58 are connected to the input of an analog amplifier 70. Analog amplifier 70 can be a conventional differential amplifier circuit for use with sensors 48, 56 and 58. The output of analog amplifier 70 is sequentially connected by an analog multiplexer 72 to the input of A/D converter 74. The output of analog amplifier 70 is a voltage which represents the respective sensed parameters. Digitized amplifier output voltages are supplied by A/D converter 74 to microprocessor 54. Microprocessor 54 may be a type 68HCII available from Motorola. However, it will be appreciated that any suitable microprocessor or general purpose digital or analog computer can be used to the parameters of temperature, voltage or current.

Microprocessor 54 sequentially receives and stores digital representations of temperature. Each digital value received by microprocessor 54 corresponds to different parameters.

Calculated power and temperature values can be indicated on user interface and display 62. Alternatively, or in addition to the numerical indication of power, calculated power values can be compared by microprocessor 54 with power limits. When the values exceed predetermined power or temperature values, a warning can be given on user interface and display 62, and additionally, the delivery of electromagnetic energy can be reduced, modified or interrupted. A control signal from microprocessor 54 can modify the power level supplied by energy source 20.

In preferred embodiment of the invention, the materials that make up the various parts of an apparatus of the invention have the following characteristics:

| Component | Tensile Strength in MPa | % Elongation | Conductivity cal/cm²/cm/sec/° C. | Resistivity nΩ * m | Melt temp. ° C. | Geometry (height, width, and/or dia.) in mm |
|---|---|---|---|---|---|---|
| Mandrel | 600-2000 | 5-100 | N/A | N/A | N/A | height 0.2-2.3 width 0.05-0.5 |
| Heating Element | 300 min. | 20 (min.) | .025-0.2 | 500-1500* | N/A | .05-0.5 dia. |
| Conductor wire | N/A | N/A | 0.2-1.0 | 150 max.* | N/A | 0.1-0.5 dia. |
| Plastic sheath | N/A | 25 (min.) | N/A | N/A | 80* (min.) | 0.05-0.2 thickness |

Another preferred characteristic is that the minimum ratio of heating element resistivity to conductor wire resistivity is 6:1; the preferred minimum ratio of guiding mandrel height to guiding mandrel width is 2:1. Tensile strength and % elongation can be measured according to ASTME8 (tension test of metallic materials). Conductivity and resistivity can be determined by procedures to be found in ASTM Vol. 2.03 for electrothermal properties.

A particularly preferred embodiment of a catheter of the invention can be prepared using a covering sheath of polyimide with an outside diameter of 1 mm and a wall thickness of 0.05 mm. Such a sheath provides a significant fraction of the stiffness and torsional strength appropriate for the catheter. Internal to the polyimide sheath and in the intradiscal section of the catheter is a heating coil of insulated nickel/chromium wire that has an outside diameter that matches the interior diameter of the polyimide sheath. This heating coil provides both heat and additional stiffness to the assembly. Also internal to the polyimide sheath on each side of the coil (longitudinally) is a 0.1 mm-walled, 304 stainless-steel, metallic band whose outer diameter matches the inner diameter of the sheath, the distal band having a hemispherical end that exits the end of the polyimide sheath and creates a blunt tip 29 at the end of the catheter. These bands provide enhanced radio-opacity for fluoroscopic visualization, as well as some of the stiffness of the assembled apparatus. Proximal to the proximal metallic band and internal to the sheath is an additional polyimide tube 47 that increases the stiffness of the catheter in the region that transitions from the intradiscal section containing the coil to the rigid proximal section. Proximal to the second polyimide tube and internal to the sheath is a 304 stainless steel (fully hard) hypodermic tube with an outside diameter matching the inside diameter of the polyimide sheath and a wall thickness of 0.1 mm. This combination provides the rigidity needed for a physician to advance the distal portion of the device inside a nucleus pulposus and provides tactile force feedback from the tip to the physician.

In some embodiments, inside the bands, coil, hypodermic tube, and both the polyimide sheath and internal polyimide tube is a guiding mandrel that extends from a proximal handle to tip. In one embodiment, this mandrel is 0.15 mm by 0.5 mm and formed from 304 stainless steel. In another embodiment, it is a 0.3 mm diameter 304 stainless steel wire, with the distal 2.5 cm flattened to 0.2 mm by 0.5 mm.

Inside the center of the heating coil is a T-type thermocouple potted with cyanoacrylate adhesive into a polyimide sheath and located alongside the mandrel. The thermocouple wire travels through the coil and hypodermic tube to the handle at the proximal end of the apparatus. Two copper conductor wires (36 gauge-insulated with polyimide) are soldered to the heating coil and pass through the hypodermic tube and handle to the proximal handle's electrical connector, which allows a power supply and feedback controls to be connected to electrical elements in the catheter. One embodiment has the handle fitted with a 1-3 meter cable extension ending in an electrical connector to eliminate the need for a connector in the handle. This design reduces weight (from connector elements) on the proximal end and increases the physician's tactile feedback during device manipulation.

The entire inside of the catheter in one embodiment is encapsulated with a silicone material which removes air (which would insulate the heat created by the heating coil) and helps support the polyimide sheath to prevent collapse (i.e., increases stiffness). Instead of the silicone, another embodiment uses an epoxy which remains flexible after curing. Strain relief is provided between the catheter body and the handle with an elastomeric boot. The distal end of the catheter is pre-bent 15-30° off the longitudinal axis of the catheter at about 5-10 mm from the distal tip.

The catheter in one embodiment carries visible markings 38 on the hypodermic tube (with the markings being visible through the polyimide sheath) to indicate distance of insertion of the catheter into an introducer and/or distance that the distal end of the catheter extends out of the introducer into a disc. The catheter is also marked both visually and with tactile relief on its handle to indicate the direction of bending of the pre-bent tip and biased stiffness.

The guidable apparatus described herein can be used in any of a number of methods to treat annular fissures. Specific methods that can be carried out with an apparatus of the invention will now be described.

Discs with fissures can be treated non-destructively with or without the removal of nucleus tissue other than limited desiccation of the nucleus pulposus which reduces its water content. Fissures can also be ameliorated by shrinking the collagen component of the surrounding annulus to bring the sides closer to their normal position. Thermal shrinkage of collagen also facilitates ingrowth of collagen which increases annular stiffness. Fissures can also be repaired with sealants such as a filler (non-adhesive material that blocks the opening) and/or bonding material (adhesives or cements) which help seal the tear. The fissure can also be treated with global heating of the disc. Most of the heat will be directed toward the fissure, but the remainder of the disc will also receive some heat.

In some methods of the invention, bonding materials such as collagen, albumin, and a mixture of fibrinogen and thrombin are delivered to the fissure. Collagen from a variety of sources can be used (e.g., bovine extracted collagen from Semex Medical, Frazer Pa., or human recombinant collagen from Collagen Corp., Palo Alto, Calif.). The collagen is injected dissolved or as a fine slurry, after which it is gradually thickens (or may be heated) in the fissure, where the injected collagen provides a matrix for collagen disposition by the body.

A variety of different materials can also be delivered to the disc, such as, for example, to the fissure, including but not limited to electrolyte solutions (i.e. normal saline), contrast media (e.g., Conray meglumine iothalamate), pharmaceutical agents (such as the steroid methylprednisolone sodium succinate available from Pharmacia & Upjohn. Kalamazoo, Mich., and nonsteroidal anti-inflammatory drugs), chemonucleolytic enzyme (e.g., chymopapain), hydrogel (such as disclosed in U.S. Pat. No. 4,478,822), osteoinductive substances (e.g., BMP, see U.S. Pat. No. 5,364,839), chondrocyte inductive substance (e.g., TGF-.beta.) and the like. The materials are delivered via the catheter and/or introducer to the disc. Preferably, however, when precision placement of the material (as in a fissure) is necessary or desired, the delivery method uses the apparatus described above, especially when delivery to the posterior, posterior lateral, or posterior medial region of the disc is desired. The materials may be administered simultaneously or sequentially, such as beginning with an electrolytic solution (which helps the physician view the pathology) and following with products to seal a fissure.

The materials are delivered in an amount sufficient to decrease the extent of the fissure at least partially, preferably to fill the fissure completely. The delivered material can be fixed in position with an adhesive, with a hydrogel that is liquid at room temperature gels at body temperature, with naturally occurring processes (such as interaction of fibrinogen and thrombin) within the disc, or by heating the disc as described in more detail below.

To seal a fissure, a combination of thrombin and fibrinogen is injected at the fissure, after which it coagulates and forms a seal over the fissure. A kit with appropriate syringes and other equipment is available from Micromedics, Inc., Eagan, Minn. Frozen fibrinogen solution is thawed in its plastic bag and then dispensed to a small med cup. Thrombin is reconstituted with sterile water in the "slow gel" concentration (100 units/ml) for tissue bonding. For example, 100 ml is added to a vial containing 10,000 units. Thrombin solution is withdrawn from the vial and dispensed to a second med cup. The two syringes are filled equally, one with each solution. Then the syringe tips are each twisted into an applicator that mixes the solutions before passing them to an administration tube. The syringes are fitted into the dual syringe holder and the plunger link, which helps the practitioner administer equal amounts of thrombin and fibrinogen. Then the practitioner connects the administration tube to the proximal end of the inventive catheter, depresses the plungers and dispenses the sealant solution to the fissure. The thrombin and fibrinogen react and form a natural seal over the fissure.

Chymopapain can be injected through the subject catheter, particularly near a herniation of the disc. Chymopapain splits side chains off proteoglycan molecules, thereby decreasing their ability to hold water and their volume. The disc gradually loses water and decreases in size. A typical dose is 0.75 to 1.0 ml (2000 pKat/ml).

In some embodiments, thermal energy is delivered to a selected section of the disc in an amount that does not create a destructive lesion to the disc, other than at most a change in the water content of the nucleus pulposus. In one embodiment there is no removal and/or vaporization of disc material positioned adjacent to an energy delivery device positioned in a nucleus pulposus. Sufficient thermal energy is delivered to the disc to change its biochemical and/or biomechanical properties without structural degradation of tissue.

Thermal energy is used to, e.g., cauterize granulation tissue which is pain sensitive and forms in a long-standing tear or fissure, and/or ablate granulation tissue. Additionally or alternatively, thermal energy is used to seal at least a part of the fissure. To do that, the disc material adjacent to the fissure is typically heated to a temperature in the range of 45-70° C. which is sufficient to shrink and weld collagen. In one method, tissue is heated to a temperature of at least 50° C. for times of approximately one, two, three minutes, or longer, as needed to shrink the tissue back into place.

Delivery of thermal energy to the nucleus pulposus removes some water and permits the nucleus pulposus to shrink. This reduces a "pushing out" effect that may have contributed to the fissure. Reducing the pressure in the disc and repairing the fissure may help stabilize the spine and reduce pain.

Fissures can also be ameliorated by shrinking the collagen component of the annulus to bring the sides of the fissure closer together in their normal position, creating a smaller annular circumference. Electromagnetic energy can be applied to heat and shrink the collagen component of the annulus fibrosus. This reduces the redundancy in the disc roll that is created in a degenerative disc. This also reduces the "pushing out" effect that created a contained herniation. The tightening and stiffening of the annulus fibrosus helps the disc function more normally. Tightening the annulus fibrosus can help stabilize the spine and relieve pain. Careful application of electromagnetic energy locally increases the stiffness of the disc in appropriate locations without overheating and harming other parts of the disc.

Electromagnetic energy also can be applied to shrink collagen in the nucleus pulposus. Delivery of electromagnetic energy to the nucleus pulposus removes some water and permits the nucleus pulposus to withdraw. This also can reduce the "pushing out" effect. Shrinking the disc, such as, for example, by shrinking of the nucleus pulposus by reducing water content, and/or tightening up the annulus fibrosus wall can create a rejuvenation of the disc. Reducing the pressure in the disc and tightening the annulus fibrosus can produce a favorable biomechanical effect.

Global heating of the disc also can be used to cauterize the granulation tissue and seal the fissure. In this embodiment of the method, the heating element is positioned away from the annulus but energy radiates to the annulus to raise the temperature of the tissue around the fissure. This global heating method can help seal a large area or multiple fissures simultaneously.

The energy delivery device can be configured to deliver sufficient energy to the intervertebral disc to provide a denervation of a nerve at a selected site of the intervertebral disc. For example, degenerative intervertebral discs with fissures can be treated by denervating selected nerves that are, for example, imbedded in the interior wall of the annulus fibrosus or that are located outside of the interior wall including those on the surface of the wall. Electromagnetic energy can be used to cauterize granulation tissue which is a pain sensitive area and formed in the annulus fibrosus wall. Sufficient thermal energy also can be delivered to selectively denervate nociceptors in and adjacent to, for example, a fissure.

All publications and patent applications mentioned in this specification are herein incorporated by reference to the same extent as if each individual publication or patent application was specifically and individually indicated to be incorporated by reference.

The foregoing description of preferred embodiments of the invention has been presented for purposes of illustration and description. It is not intended to be exhaustive or to limit the invention to the precise forms disclosed. Many modifications and variations will be apparent to practitioners skilled in this art. It is intended that the scope of the invention be defined by the following claims and their equivalents.

A number of embodiments have been described. Nevertheless, it will be understood that various modifications may be made. Accordingly, other embodiments are within the scope of the following claims.

What is claimed is:

1. A method of treating an intervertebral disc, the method comprising:
    inserting an introducer into an intervertebral disc having a contained disc herniation;
    inserting a catheter through the introducer and into the intervertebral disc;
    advancing a distal region of the catheter through a nucleus pulposus of the intervertebral disc to an inner wall of an annulus fibrosus by blunt dissection;
    delivering radiofrequency ("RF") energy to material of the intervertebral disc using an electrode disposed at the distal region of the catheter; and
    removing the material with the delivered RF energy, wherein removing material with the delivered RF energy reduces pressure in the intervertebral disc to treat the disc herniation.

2. The method of claims 1 wherein removing the material comprises removing water.

3. The method of claim 1 wherein removing the material with the delivered RF energy comprises ablating the material.

4. The method of claim 1 or 3 wherein removing the material comprises removing disc tissue.

5. The method of claim 1, 2, or 3 wherein advancing the distal region of the catheter through the nucleus pulposus comprises advancing the distal region along a curved path.

6. The method of claim 1, 2, or 3 wherein the introducer comprises a needle and inserting the introducer comprises inserting the needle.

7. The method of claim 6 further comprising inserting the needle and a trocar.

8. The method of claim 6 wherein inserting a needle comprises inserting a 17-gauge needle.

9. The method of claim 8 further comprising inserting the needle and a trocar.

10. The method of claim 1, 2, or 3 further comprising providing the catheter with a total length between 5 and 24 inches.

11. The method of claim 1, 2, or 3 wherein advancing the distal region of the catheter comprises advancing the catheter so that a maximum distance the catheter extends from the introducer is no greater than one and one-half times the circumference of the nucleus pulposus.

12. The method of claim 1, 2, or 3 wherein delivering RF energy comprises delivering RF energy from a bipolar electrode configuration.

13. The method of claim 1, 2, or 3 further comprising twisting the catheter after inserting the catheter into the intervertebral disc.

14. The method of claim 13 wherein advancing the distal region of the catheter through the nucleus pulposus comprises advancing the distal region along a curved path.

15. The method of claim 1, 2, or 3 further comprising heating the material to a temperature in a range of 45-70 degrees C. with the delivered RF energy.

16. The method of claims 1, 2, or 3 further comprising heating the material to a temperature of 55 degrees C. with the delivered RF energy.

17. The method of claims 1, 2, or 3 further comprising heating the material to a temperature of 65 degrees C. with the delivered RF energy.

18. The method of claim 1, 2, or 3 further comprising denervating at least a portion of the intervertebral disc with the delivered RF energy.

19. The method of claim 1, 2, or 3 wherein advancing the distal region comprises advancing the electrode beyond the introducer.

20. The method of claim 1, 2, or 3 wherein delivering RF energy comprises delivering RF energy to the inner wall of the annulus fibrosus.

21. The method of claim 1, 2, or 3 wherein delivering RF energy comprises delivering RF energy while the catheter is positioned at a location adjacent the inner wall of the annulus fibrosus.

22. The method of claim 1, 2, or 3 wherein delivering RF energy comprises delivering RF energy to multiple locations in the intervertebral disc using at least the electrode.

23. The method of claim 22 wherein delivering RF energy to multiple locations comprises delivering RF energy to the multiple locations simultaneously.

24. The method of claim 22 wherein delivering RF energy to multiple locations comprises:
    delivering RF energy to at least a first of the multiple locations using the electrode; and
    delivering RF energy to at least a second of the multiple locations using a second electrode.

25. The method of claim 22 wherein delivering RF energy to multiple locations comprises delivering RF energy to the multiple locations serially.

26. The method of claim 22 wherein delivering RF energy to multiple locations comprises delivering RF energy to the multiple locations using the electrode.

27. The method of claim 1, 2, or 3 further comprising advancing the catheter along the inner wall of the annulus fibrosus.

28. The method of claim 1 wherein advancing the distal region of the catheter comprises conforming the catheter sufficiently to the inner wall of the annulus fibrosus to contact multiple locations on the inner wall.

* * * * *